(12) United States Patent
Liu

(10) Patent No.: US 11,938,215 B2
(45) Date of Patent: Mar. 26, 2024

(54) METHOD FOR OPERATING A BENEFIT AGENT DELIVERY SYSTEM COMPRISING MICROCELLS HAVING AN ELECTRICALLY ERODING SEALING LAYER

(71) Applicant: E INK CORPORATION, Billerica, MA (US)

(72) Inventor: Lei Liu, Fremont, CA (US)

(73) Assignee: E INK CORPORATION, Billerica, MA (US)

( * ) Notice: Subject to any disclaimer, the term of this patent is extended or adjusted under 35 U.S.C. 154(b) by 0 days.

(21) Appl. No.: 18/159,611

(22) Filed: Jan. 25, 2023

(65) Prior Publication Data
US 2023/0165787 A1 Jun. 1, 2023

Related U.S. Application Data

(62) Division of application No. 16/952,433, filed on Nov. 19, 2020.

(Continued)

(51) Int. Cl.
*A61K 9/00* (2006.01)
*A61K 9/70* (2006.01)
*A61M 37/00* (2006.01)

(52) U.S. Cl.
CPC ............ *A61K 9/0009* (2013.01); *A61K 9/703* (2013.01); *A61M 37/00* (2013.01);
(Continued)

(58) Field of Classification Search
CPC ..... A61K 9/0009; A61K 9/703; A61M 37/00; A61M 2037/0007; A61M 2205/0216;
(Continued)

(56) References Cited

U.S. PATENT DOCUMENTS 3,756,693 A 9/1973 Ota
3,892,568 A 7/1975 Ota
(Continued)

FOREIGN PATENT DOCUMENTS

CN 1705907 A 12/2005
EP 1457233 A1 9/2004
(Continued)

OTHER PUBLICATIONS

Harvey, T.G.; "Replication techniques for micro-optics"; SPIE Proc. vol. 3099, pp. 76-82; 1997. Jan. 1, 1997.
(Continued)

*Primary Examiner* — Brandy S Lee
*Assistant Examiner* — Fatimata Sahra Diop
(74) *Attorney, Agent, or Firm* — Ioannis Constantinides

(57) ABSTRACT

A benefit agent delivery system whereby benefit agents can be delivered on demand and/or a variety of different benefit agents at different concentrations can be delivered from the same system. The benefit agent delivery system includes a microcell layer comprising a plurality of microcells, wherein the microcells are filled with a carrier and a benefit agent. The microcells include an opening, wherein the opening is spanned by a sealing layer comprising a polymer and metallic material. Application of an electric field across the microcell layer and the sealing layer results in the migration of the metallic material from the sealing layer and the creation of a porous sealing layer, allowing the benefit agent to be released from the benefit agent delivery system.

17 Claims, 16 Drawing Sheets

Related U.S. Application Data

(60) Provisional application No. 62/941,216, filed on Nov. 27, 2019.

(52) U.S. Cl.
CPC ............... *A61M 2037/0007* (2013.01); *A61M 2205/0216* (2013.01); *A61M 2205/0233* (2013.01); *A61M 2205/0238* (2013.01); *A61M 2207/10* (2013.01)

(58) Field of Classification Search
CPC .. A61M 2205/0233; A61M 2205/0238; A61M 2207/10; A61M 35/10; A61M 35/00; A61M 2205/055; A61N 1/0428
See application file for complete search history.

(56) References Cited

U.S. PATENT DOCUMENTS

| | | |
|---|---|---|
| 4,298,448 A | 11/1981 | Muller et al. |
| 4,559,222 A | 12/1985 | Enscore et al. |
| 4,640,689 A | 2/1987 | Sibalis |
| 4,734,090 A | 3/1988 | Sibalis |
| 5,002,527 A | 3/1991 | Reller et al. |
| 5,125,894 A | 6/1992 | Phipps et al. |
| 5,135,479 A | 8/1992 | Sibalis et al. |
| 5,158,537 A | 10/1992 | Haak et al. |
| 5,378,574 A | 1/1995 | Winnik et al. |
| 5,380,271 A | 1/1995 | Gyory |
| 5,486,362 A | 1/1996 | Kitchell et al. |
| 5,533,995 A | 7/1996 | Corish et al. |
| 5,591,767 A | 1/1997 | Mohr et al. |
| 5,603,693 A | 2/1997 | Frenkel et al. |
| 5,658,592 A | 8/1997 | Tanihara et al. |
| 5,797,898 A | 8/1998 | Santini, Jr. et al. |
| 5,931,804 A | 8/1999 | Sibalis |
| 5,980,719 A | 11/1999 | Cherukuri et al. |
| 5,980,943 A | 11/1999 | Ayer et al. |
| 6,017,584 A | 1/2000 | Albert et al. |
| 6,123,861 A | 9/2000 | Santini, Jr. et al. |
| 6,198,809 B1 | 3/2001 | DiSanto |
| 6,337,761 B1 | 1/2002 | Rogers |
| 6,373,461 B1 | 4/2002 | Hasegawa et al. |
| 6,486,866 B1 | 11/2002 | Kuwahara et al. |
| 6,491,666 B1 | 12/2002 | Santini, Jr. et al. |
| 6,517,618 B2 | 2/2003 | Foucher et al. |
| 6,521,191 B1 | 2/2003 | Schenk et al. |
| 6,525,866 B1 | 2/2003 | Lin et al. |
| 6,538,801 B2 | 3/2003 | Jacobson et al. |
| 6,545,797 B2 | 4/2003 | Chen et al. |
| 6,564,093 B1 | 5/2003 | Ostrow et al. |
| 6,565,532 B1 | 5/2003 | Yuzhakov et al. |
| 6,600,534 B1 | 7/2003 | Tanaka et al. |
| 6,650,462 B2 | 11/2003 | Katase |
| 6,664,944 B1 | 12/2003 | Albert et al. |
| 6,680,726 B2 | 1/2004 | Gordon, II et al. |
| 6,693,620 B1 | 2/2004 | Herb et al. |
| 6,704,133 B2 | 3/2004 | Gates et al. |
| 6,724,521 B2 | 4/2004 | Nakao et al. |
| 6,729,718 B2 | 5/2004 | Goto et al. |
| 6,751,007 B2 | 6/2004 | Liang et al. |
| 6,751,008 B2 | 6/2004 | Liang et al. |
| 6,757,560 B1 | 6/2004 | Fischer et al. |
| 6,781,745 B2 | 8/2004 | Chung et al. |
| 6,788,452 B2 | 9/2004 | Liang et al. |
| 6,829,078 B2 | 12/2004 | Liang et al. |
| 6,850,357 B2 | 2/2005 | Kaneko et al. |
| 6,864,875 B2 | 3/2005 | Drzaic et al. |
| 6,876,486 B2 | 4/2005 | Hiraoka et al. |
| 6,914,714 B2 | 7/2005 | Chen et al. |
| 6,930,818 B1 | 8/2005 | Liang et al. |
| 6,933,098 B2 | 8/2005 | Chan-Park et al. |
| 6,947,203 B2 | 9/2005 | Kanbe |
| 6,967,762 B2 | 11/2005 | Machida et al. |
| 6,972,893 B2 | 12/2005 | Chen et al. |
| 6,980,855 B2 | 12/2005 | Cho |
| 6,987,503 B2 | 1/2006 | Inoue |
| 6,987,605 B2 | 1/2006 | Liang et al. |
| 7,009,756 B2 | 3/2006 | Kishi et al. |
| 7,019,889 B2 | 3/2006 | Katase |
| 7,034,987 B2 | 4/2006 | Schlangen |
| 7,038,655 B2 | 5/2006 | Herb et al. |
| 7,038,656 B2 | 5/2006 | Liang et al. |
| 7,038,670 B2 | 5/2006 | Liang et al. |
| 7,046,228 B2 | 5/2006 | Liang et al. |
| 7,050,218 B2 | 5/2006 | Kanbe |
| 7,052,571 B2 | 5/2006 | Wang et al. |
| 7,057,600 B2 | 6/2006 | Goden |
| 7,057,798 B2 | 6/2006 | Ukigaya |
| 7,075,502 B1 | 7/2006 | Drzaic et al. |
| 7,116,466 B2 | 10/2006 | Whitesides et al. |
| 7,167,155 B1 | 1/2007 | Albert et al. |
| 7,226,550 B2 | 6/2007 | Hou et al. |
| 7,229,556 B1 | 6/2007 | Hinds, III |
| 7,259,744 B2 | 8/2007 | Arango et al. |
| 7,271,947 B2 | 9/2007 | Liang et al. |
| 7,279,064 B2 | 10/2007 | Daniel et al. |
| 7,283,119 B2 | 10/2007 | Kishi |
| 7,292,386 B2 | 11/2007 | Kanbe |
| 7,303,818 B2 | 12/2007 | Minami |
| 7,304,987 B1 | 12/2007 | James et al. |
| 7,312,916 B2 | 12/2007 | Pullen et al. |
| 7,315,758 B2 | 1/2008 | Kwiatkowski et al. |
| 7,342,556 B2 | 3/2008 | Oue et al. |
| 7,345,810 B2 | 3/2008 | Chopra et al. |
| 7,352,353 B2 | 4/2008 | Albert et al. |
| 7,365,732 B2 | 4/2008 | Matsuda et al. |
| 7,382,351 B2 | 6/2008 | Kishi |
| 7,383,083 B2 | 6/2008 | Fischer et al. |
| 7,385,751 B2 | 6/2008 | Chen et al. |
| 7,392,080 B2 | 6/2008 | Eppstein et al. |
| 7,411,719 B2 | 8/2008 | Paolini, Jr. et al. |
| 7,417,787 B2 | 8/2008 | Chopra et al. |
| 7,420,549 B2 | 9/2008 | Jacobson et al. |
| 7,433,113 B2 | 10/2008 | Chopra et al. |
| 7,443,570 B2 | 10/2008 | Chopra et al. |
| 7,474,295 B2 | 1/2009 | Matsuda |
| 7,492,505 B2 | 2/2009 | Liang et al. |
| 7,495,821 B2 | 2/2009 | Yamakita et al. |
| 7,502,162 B2 | 3/2009 | Lin et al. |
| 7,537,590 B2 | 5/2009 | Santini, Jr. et al. |
| 7,545,557 B2 | 6/2009 | Iftime et al. |
| 7,548,291 B2 | 6/2009 | Lee et al. |
| 7,557,981 B2 | 7/2009 | Liang et al. |
| 7,580,025 B2 | 8/2009 | Nakai et al. |
| 7,604,628 B2 | 10/2009 | Santini, Jr. et al. |
| 7,605,972 B2 | 10/2009 | Kawai et al. |
| 7,609,435 B2 | 10/2009 | Moriyama et al. |
| 7,611,481 B2 | 11/2009 | Cleary et al. |
| 7,626,185 B2 | 12/2009 | Krak et al. |
| 7,636,076 B2 | 12/2009 | Hung et al. |
| 7,652,656 B2 | 1/2010 | Chopra et al. |
| 7,656,576 B2 | 2/2010 | Suwabe et al. |
| 7,667,684 B2 | 2/2010 | Jacobson et al. |
| 7,679,599 B2 | 3/2010 | Kawai |
| 7,684,108 B2 | 3/2010 | Wang et al. |
| 7,686,463 B2 | 3/2010 | Goto |
| 7,715,088 B2 | 5/2010 | Liang et al. |
| 7,760,419 B2 | 7/2010 | Lee |
| 7,782,292 B2 | 8/2010 | Miyasaka et al. |
| 7,791,789 B2 | 9/2010 | Albert et al. |
| 7,800,813 B2 | 9/2010 | Wu et al. |
| 7,808,696 B2 | 10/2010 | Lee et al. |
| 7,821,702 B2 | 10/2010 | Liang et al. |
| 7,830,592 B1 | 11/2010 | Sprague et al. |
| 7,839,564 B2 | 11/2010 | Whitesides et al. |
| 7,848,009 B2 | 12/2010 | Machida et al. |
| 7,852,547 B2 | 12/2010 | Kim |
| 7,852,548 B2 | 12/2010 | Roh |
| 7,892,221 B2 | 2/2011 | Santini, Jr. et al. |
| 7,907,327 B2 | 3/2011 | Jang et al. |
| 7,910,175 B2 | 3/2011 | Webber |
| 7,911,681 B2 | 3/2011 | Ikegami et al. |
| 7,952,790 B2 | 5/2011 | Honeyman et al. |

(56) References Cited

U.S. PATENT DOCUMENTS

| | | |
|---|---|---|
| 7,956,841 B2 | 6/2011 | Albert et al. |
| 7,982,941 B2 | 7/2011 | Lin et al. |
| 8,040,594 B2 | 10/2011 | Paolini, Jr. et al. |
| 8,054,526 B2 | 11/2011 | Bouchard |
| 8,067,305 B2 | 11/2011 | Zafiropoulo et al. |
| 8,072,675 B2 | 12/2011 | Lin et al. |
| 8,081,375 B2 | 12/2011 | Komatsu et al. |
| 8,089,686 B2 | 1/2012 | Addington et al. |
| 8,095,213 B1 | 1/2012 | Sexton |
| 8,098,418 B2 | 1/2012 | Paolini, Jr. et al. |
| 8,115,729 B2 | 2/2012 | Danner et al. |
| 8,120,838 B2 | 2/2012 | Lin et al. |
| 8,159,636 B2 | 4/2012 | Sun et al. |
| 8,164,823 B2 | 4/2012 | Ikegami et al. |
| 8,169,690 B2 | 5/2012 | Lin et al. |
| 8,174,492 B2 | 5/2012 | Kim et al. |
| 8,213,076 B2 | 7/2012 | Albert et al. |
| 8,237,892 B1 | 8/2012 | Sprague et al. |
| 8,243,013 B1 | 8/2012 | Sprague et al. |
| 8,257,324 B2 | 9/2012 | Prausnitz et al. |
| 8,355,196 B2 | 1/2013 | Yan et al. |
| 8,363,299 B2 | 1/2013 | Paolini, Jr. et al. |
| 8,395,836 B2 | 3/2013 | Lin |
| 8,403,915 B2 | 3/2013 | Santini, Jr. et al. |
| 8,422,116 B2 | 4/2013 | Sprague et al. |
| 8,440,222 B2 | 5/2013 | Hausner et al. |
| 8,441,713 B2 | 5/2013 | Kawashima et al. |
| 8,441,714 B2 | 5/2013 | Paolini, Jr. et al. |
| 8,441,716 B2 | 5/2013 | Paolini, Jr. et al. |
| 8,466,852 B2 | 6/2013 | Drzaic et al. |
| 8,477,404 B2 | 7/2013 | Moriyama et al. |
| 8,477,405 B2 | 7/2013 | Ishii et al. |
| 8,503,063 B2 | 8/2013 | Sprague |
| 8,517,958 B2 | 8/2013 | Eppstein et al. |
| 8,520,296 B2 | 8/2013 | Wang et al. |
| 8,537,104 B2 | 9/2013 | Markvoort et al. |
| 8,565,522 B2 | 10/2013 | Swic |
| 8,570,272 B2 | 10/2013 | Hsieh et al. |
| 8,570,639 B2 | 10/2013 | Masuzawa et al. |
| 8,574,937 B2 | 11/2013 | Shi |
| 8,576,470 B2 | 11/2013 | Paolini, Jr. et al. |
| 8,576,475 B2 | 11/2013 | Huang et al. |
| 8,593,721 B2 | 11/2013 | Albert et al. |
| 8,599,120 B2 | 12/2013 | Kanou |
| 8,605,354 B2 | 12/2013 | Zhang et al. |
| 8,610,998 B2 | 12/2013 | Baisch et al. |
| 8,629,832 B2 | 1/2014 | Tanabe |
| 8,649,084 B2 | 2/2014 | Wang et al. |
| 8,670,174 B2 | 3/2014 | Sprague et al. |
| 8,674,978 B2 | 3/2014 | Komatsu et al. |
| 8,681,191 B2 | 3/2014 | Yang et al. |
| 8,687,265 B2 | 4/2014 | Ahn et al. |
| 8,696,637 B2 | 4/2014 | Ross |
| 8,704,754 B2 | 4/2014 | Machida et al. |
| 8,704,756 B2 | 4/2014 | Lin |
| 8,717,662 B2 | 5/2014 | Komatsu |
| 8,717,664 B2 | 5/2014 | Wang et al. |
| 8,744,569 B2 | 6/2014 | Imran |
| 8,786,935 B2 | 7/2014 | Sprague |
| 8,797,258 B2 | 8/2014 | Sprague |
| 8,797,634 B2 | 8/2014 | Paolini, Jr. et al. |
| 8,797,636 B2 | 8/2014 | Yang et al. |
| 8,797,637 B2 | 8/2014 | Fujishiro et al. |
| 8,810,899 B2 | 8/2014 | Sprague et al. |
| 8,830,559 B2 | 9/2014 | Honeyman et al. |
| 8,830,561 B2 | 9/2014 | Zang et al. |
| 8,862,223 B2 | 10/2014 | Yanaki |
| 8,873,129 B2 | 10/2014 | Paolini, Jr. et al. |
| 8,902,153 B2 | 12/2014 | Bouchard et al. |
| 8,902,491 B2 | 12/2014 | Wang et al. |
| 8,917,439 B2 | 12/2014 | Wang et al. |
| 8,962,014 B2 | 2/2015 | Prinz et al. |
| 8,964,282 B2 | 2/2015 | Wang et al. |
| 8,968,699 B2 | 3/2015 | Jin et al. |
| 8,976,444 B2 | 3/2015 | Zhang et al. |
| 9,013,783 B2 | 4/2015 | Sprague |
| 9,052,564 B2 | 6/2015 | Sprague et al. |
| 9,116,412 B2 | 8/2015 | Lin |
| 9,140,952 B2 | 9/2015 | Sprague et al. |
| 9,146,439 B2 | 9/2015 | Zhang |
| 9,164,207 B2 | 10/2015 | Honeyman et al. |
| 9,170,467 B2 | 10/2015 | Whitesides et al. |
| 9,170,468 B2 | 10/2015 | Lin et al. |
| 9,182,646 B2 | 11/2015 | Paolini, Jr. et al. |
| 9,186,317 B2 | 11/2015 | Smyth et al. |
| 9,188,829 B2 | 11/2015 | Li et al. |
| 9,195,111 B2 | 11/2015 | Anseth et al. |
| 9,199,441 B2 | 12/2015 | Danner |
| 9,251,736 B2 | 2/2016 | Lin et al. |
| 9,268,191 B2 | 2/2016 | Paolini, Jr. et al. |
| 9,285,649 B2 | 3/2016 | Du et al. |
| 9,293,511 B2 | 3/2016 | Jacobson et al. |
| 9,320,720 B2 | 4/2016 | Maier |
| 9,326,979 B2 | 5/2016 | Kimura et al. |
| 9,327,105 B2 | 5/2016 | Ramdas et al. |
| 9,341,916 B2 | 5/2016 | Telfer et al. |
| 9,360,733 B2 | 6/2016 | Wang et al. |
| 9,361,836 B1 | 6/2016 | Telfer et al. |
| 9,383,623 B2 | 7/2016 | Lin et al. |
| 9,388,307 B2 | 7/2016 | Li et al. |
| 9,423,666 B2 | 8/2016 | Wang et al. |
| 9,459,510 B2 | 10/2016 | Lin |
| 9,460,666 B2 | 10/2016 | Sprague et al. |
| 9,513,527 B2 | 12/2016 | Chan et al. |
| 9,541,814 B2 | 1/2017 | Lin et al. |
| 9,610,440 B2 | 4/2017 | Jordan et al. |
| 9,671,668 B2 | 6/2017 | Chan et al. |
| 9,697,778 B2 | 7/2017 | Telfer et al. |
| 9,740,076 B2 | 8/2017 | Paolini, Jr. et al. |
| 9,759,978 B2 | 9/2017 | Liu |
| 9,759,980 B2 | 9/2017 | Du et al. |
| 9,812,073 B2 | 11/2017 | Lin et al. |
| 9,931,296 B2 | 4/2018 | Doshi |
| 9,968,549 B2 | 5/2018 | Kosel et al. |
| 10,036,931 B2 | 7/2018 | Chan et al. |
| 10,087,344 B2 | 10/2018 | Moran |
| 10,162,242 B2 | 12/2018 | Wang et al. |
| 10,209,556 B2 | 2/2019 | Rosenfeld et al. |
| 10,332,435 B2 | 6/2019 | Wang et al. |
| 10,514,583 B2 | 12/2019 | Zhang |
| 10,646,454 B2 | 5/2020 | Liu et al. |
| 10,761,395 B2 | 9/2020 | Du et al. |
| 10,918,846 B2 | 2/2021 | Nagai et al. |
| 10,933,029 B2 | 3/2021 | Liu |
| 11,266,832 B2 | 3/2022 | Liu |
| 2001/0023330 A1 | 9/2001 | Palti |
| 2001/0035926 A1 | 11/2001 | Yamaguchi et al. |
| 2004/0085619 A1 | 5/2004 | Wu et al. |
| 2005/0191337 A1 | 9/2005 | Gueret |
| 2006/0009731 A1 | 1/2006 | Wu et al. |
| 2006/0188558 A1 | 8/2006 | Jackson et al. |
| 2006/0257450 A1 | 11/2006 | Mudumba et al. |
| 2006/0269475 A1 | 11/2006 | Ryu et al. |
| 2007/0002008 A1 | 1/2007 | Tam |
| 2007/0080928 A1 | 4/2007 | Ishii et al. |
| 2007/0083186 A1 | 4/2007 | Carter et al. |
| 2007/0196456 A1 | 8/2007 | Stevens et al. |
| 2007/0232983 A1 | 10/2007 | Smith |
| 2007/0248657 A1 | 10/2007 | Smith et al. |
| 2007/0273637 A1 | 11/2007 | Zhou et al. |
| 2007/0292463 A1 | 12/2007 | Spector |
| 2008/0020007 A1 | 1/2008 | Zang |
| 2008/0042928 A1 | 2/2008 | Schlangen et al. |
| 2008/0043318 A1 | 2/2008 | Whitesides et al. |
| 2008/0048970 A1 | 2/2008 | Drzaic et al. |
| 2008/0062159 A1 | 3/2008 | Roh et al. |
| 2008/0117165 A1 | 5/2008 | Machida et al. |
| 2008/0174531 A1 | 7/2008 | Sah |
| 2009/0153942 A1 | 6/2009 | Daniel et al. |
| 2009/0167754 A1 | 7/2009 | Hatta |
| 2009/0184897 A1 | 7/2009 | Miyamoto |
| 2009/0225398 A1 | 9/2009 | Duthaler et al. |
| 2009/0234214 A1 | 9/2009 | Santini, Jr. et al. |
| 2009/0311484 A1 | 12/2009 | Mclellan et al. |

(56) References Cited

U.S. PATENT DOCUMENTS

| | | |
|---|---|---|
| 2010/0030129 A1 | 2/2010 | Nitzan et al. |
| 2010/0156780 A1 | 6/2010 | Jacobson et al. |
| 2010/0189793 A1 | 7/2010 | Meyer et al. |
| 2010/0331811 A1 | 12/2010 | Imran |
| 2011/0043543 A1 | 2/2011 | Chen et al. |
| 2011/0046557 A1 | 2/2011 | Lee et al. |
| 2011/0111013 A1 | 5/2011 | Salman et al. |
| 2011/0175939 A1 | 7/2011 | Moriyama et al. |
| 2011/0196474 A1 | 8/2011 | Davalian et al. |
| 2011/0199671 A1 | 8/2011 | Amundson et al. |
| 2011/0217639 A1 | 9/2011 | Sprague |
| 2011/0234557 A1 | 9/2011 | Yang et al. |
| 2012/0017663 A1 | 1/2012 | Schreiber et al. |
| 2012/0299947 A1 | 11/2012 | Tsuda et al. |
| 2012/0326957 A1 | 12/2012 | Drzaic et al. |
| 2013/0096486 A1 | 4/2013 | Schroeder et al. |
| 2013/0242378 A1 | 9/2013 | Paolini, Jr. et al. |
| 2013/0278995 A1 | 10/2013 | Drzaic et al. |
| 2014/0009818 A1 | 1/2014 | Brochon et al. |
| 2014/0011913 A1 | 1/2014 | Du et al. |
| 2014/0055840 A1 | 2/2014 | Zang et al. |
| 2014/0078576 A1 | 3/2014 | Sprague |
| 2014/0330223 A1 | 11/2014 | Schurad et al. |
| 2014/0362213 A1 | 12/2014 | Tseng |
| 2015/0005720 A1 | 1/2015 | Zang et al. |
| 2015/0018749 A1 | 1/2015 | Faupel et al. |
| 2015/0118390 A1 | 4/2015 | Rosenfeld et al. |
| 2015/0167184 A1 | 6/2015 | Abhishek et al. |
| 2015/0268531 A1 | 9/2015 | Wang et al. |
| 2015/0301246 A1 | 10/2015 | Zang et al. |
| 2015/0301425 A1 | 10/2015 | Du et al. |
| 2016/0045158 A1 | 2/2016 | Hsu |
| 2016/0048054 A1 | 2/2016 | Danner |
| 2016/0279072 A1 | 9/2016 | Li et al. |
| 2017/0119960 A1* | 5/2017 | Dang .............. A61M 5/14276 |
| 2017/0205649 A1 | 7/2017 | Wang et al. |
| 2018/0271799 A1* | 9/2018 | Liu .................... A61K 9/0009 |
| 2018/0271800 A1 | 9/2018 | Liu et al. |
| 2018/0272114 A1 | 9/2018 | Liu et al. |
| 2019/0142763 A1 | 5/2019 | Liu |

FOREIGN PATENT DOCUMENTS

| | | |
|---|---|---|
| JP | 2006343458 A | 12/2006 |
| JP | 2007033710 A | 2/2007 |
| JP | 2008033000 A | 2/2008 |
| JP | 2008209589 A | 9/2008 |
| JP | 2009116041 A | 5/2009 |
| JP | 2009192637 A | 8/2009 |
| JP | 2009244635 A | 10/2009 |
| JP | 2010044114 A | 2/2010 |
| JP | 2010210856 A | 9/2010 |
| JP | 2011158783 A | 8/2011 |
| JP | 2015151380 A | 8/2015 |
| KR | 19980025307 A | 7/1998 |
| KR | 20070082680 A | 8/2007 |
| KR | 20110103765 A | 9/2011 |
| KR | 20190122531 A | 10/2019 |
| TW | 201122697 A | 7/2011 |
| TW | 201237529 A | 9/2012 |
| WO | 1999053373 A1 | 10/1999 |
| WO | 2009073686 A1 | 6/2009 |

OTHER PUBLICATIONS

Seigou Kawaguchi et al., "Synthesis of polyethylene macromonomers and their radical copolymerizations with methyl methacrylate in homogeneous and oligoethylene melts media" Designed Monomers and Polymers 2000, vol. 3, No. 3. p. 263-277 Jan. 1, 2000.

Korean Intellectual Property Office; PCT/US2015/011237; International Search Report and Written Opinion ; dated Apr. 10, 2015, dated Apr. 10, 2015.

European Patent Office; EP Appl. No. 15737734.2; Extended European Search Report; dated Jun. 6, 2017, dated Jun. 6, 2017.

Ebbert Jon O. et al., "Combination Pharmacotherapy for Stopping Smoking: What Advantages Does it Offer?", Drugs, vol. 70 No. 6, pp. 643-650, (Apr. 16, 2010). Apr. 16, 2010.

Kaiyong Cai et al., "Magnetically triggered reversible Controlled Drug Delivery from Microfabricated Polymeric Multireservior Devices"., Advanced Materials. 2009, 21, 4045-4049 May 28, 2009.

Korean Intellectual Property Office, PCT/US2018/023917, International Search Report and Written Opinion, dated Jul. 10, 2017, dated Jul. 10, 2018.

Korean Intellectual Property Office, PCT/US2018/023928, International Search Report and Written Opinion, dated Jul. 10, 2018, dated Jul. 10, 2018.

Korean Intellectual Property Office, PCT/US2018/023921, International Search Report and Written Opinion, dated Jul. 10, 2018, dated Jul. 10, 2018.

Korean Intellectual Property Office, PCT/US2018/060259, International Search Report and Written Opinion, dated Apr. 29, 2019, dated Apr. 29, 2019.

Korean Intellectual Property Office, PCT/US2018/060266, International Search Report and Written Opinion, dated Apr. 29, 2019, dated Apr. 29, 2019.

Xuan, Shouhu et al., "Systhesis of Fe3O4@Polyaniline Core/Shell Microspheres with Well-Defined Blackberrym-Like Morphology", J. Phys. Chem. C., vol. 112, pp. 18804-9. (2008). Oct. 3, 2008.

Sahoo et al., "A Review of Transdermal drug delivery system", Journal der Pharmazie Forschung, vol. 2, N-1, 2013, 32-56 (2013) 2013.

Huang, W. C. et al.. , "A flexible drug delivery chip for the magnetically-controlled release of anti-epileptic drugs", Journal of Controlled Release, vol. 139, Issue 3, Nov. 3, 2009, pp. 221-228 Nov. 3, 2009.

European Patent Office, EP Appl. No 18771343.3, Extended European Search Report, dated Aug. 14, 2020, dated Aug. 14, 2020.

Gulati Gaurav Kumar et al., " Programmable carbon nanotube membrane-based transdermal nicotine delivery with microdialysis validation assay", Nanomedicine: Nanotechnology, Biology and medicine, Elsevier, NL, vol. 13, No. 1, Jul. 18, 2016, p. 1-9, XP029879755, ISSN: 1549-9634 (Jul. 18, 2016) Jul. 18, 2016.

Im J S et al., " The effect of carbon nanotubes on drug delivery in an electro-sensitive transdermal drug delivery system" Biomaterials, Elsevier, Amsterdam, NL, vol. 31, No. 6, Feb. 1, 2010, pp. 1414-1419, XP026814171, ISSN: 0142-9612 (Feb. 1, 2010) Feb. 1, 2010.

European Patent Office, EP. Appl. No. 18772394.5, European Search Report, dated Nov. 30, 2020, dated Nov. 30, 2020.

European Patent Office, EP. Appl. No. 18771792.1, Supplemental Partial European Search Report, dated Nov. 24, 2020, dated Nov. 24, 2020.

European Patent Office, EP Appl. No 18878337.7, Extended European Search Report, dated Feb. 8, 2021. dated Feb. 8, 2021.

Korean Intellectual Property Office, PCT/US2020/061253, International Search Report and Written Opinion, dated Mar. 9, 2021, dated Mar. 9, 2021.

European Patent Office, EP. Appl. No. 18771792.1, Extended European Search Report, dated Mar. 31, 2021 dated Mar. 31, 2021.

European Patent Office, "European Search Report", EP Appl. No. 18879750.0, dated Jul. 27, 2021, dated Jul. 27, 2021.

European Patent Office, "Extended European Search Report", EP Appl No. 20894183.1-1122, dated Oct. 30, 2023, dated Oct. 30, 2023.

* cited by examiner

METHOD FOR OPERATING A BENEFIT AGENT DELIVERY SYSTEM COMPRISING MICROCELLS HAVING AN ELECTRICALLY ERODING SEALING LAYER

CROSS-REFERENCE TO RELATED APPLICATIONS

This application is a divisional of co-pending U.S. patent application Ser. No. 16/952,433 filed on Nov. 19, 2020 (Publication No. US20210154133 A1), which claims priority to U.S. Provisional Application No. 62/941,216 filed on Nov. 27, 2019, which is incorporated herein by reference in its entirety.

BACKGROUND OF THE INVENTION

The development of methodologies for controlled and extended release of benefit agents have attracted significant attention during the last decades. This is true for a large variety of benefit agents including pharmaceutical, nutraceutical agents, agricultural nutrients and related substances, cosmetic agents, fragrances, air care agents, and many other benefit agents in a variety of fields. Transdermal delivery of pharmaceutical agents has proven effective for drugs that are able to move across the skin barrier. For example, small amounts of nicotine can be delivered over extended periods with transdermal patches that suspend the nicotine in an ethylene vinyl acetate (EVA) copolymer. See, e.g., Nicoderm-CQ® by GlaxoSmithKline (Brentford, UK). Other examples include extended release of fragrances and malodor removing agents for improving the air quality in living spaces and automobiles, fertilizers in the soil for more efficient food production, and biocides on surfaces for mitigating microorganism growth. Controlled and extended release delivery systems may involve the delivery of various benefit agents in different forms, such as solid, liquid and gas, to different locations, and under different conditions.

A variety of delivery systems has been developed during the last decades that provide on demand delivery of benefit agents. For instance, Chrono Therapeutics (Hayward, CA) is currently testing a micro pump-enabled smart transdermal patch for delivering nicotine. Nonetheless, the corresponding device is large and visible through clothing as a sizeable bump. Thus, there remains a need for small, simle, inexpensive, versatile and safe delivery systems for delivering benefit agents on demand.

SUMMARY OF THE INVENTION

The invention addresses this need by providing a low power delivery system whereby a benefit agent or a mixture of benefit agents can be released on demand. Additionally, as described below, the invention provides a system for delivering varying amounts of benefit agents from the same delivery system at different times, and for delivering multiple benefit agents at the same or different times from the same benefit agent delivery system.

In one aspect, the invention is a benefit agent delivery system comprising a conductive layer, a microcell layer comprising a plurality of microcells, wherein each microcell includes an opening, a sealing layer spanning the opening of each microcell, and an electrode layer. A medium, comprising a carrier and a benefit agent, is contained in the plurality of microcells.

The sealing layer comprises a polymeric material and a metallic material. The conductive layer, the microcell layer, the sealing layer, and the electrode layer are vertically stacked on each other. The conductive layer, the microcell layer, the sealing layer and the electrode layer may be vertically stacked upon each other in this order. The plurality of microcells and the sealing layer are disposed between the conductive layer and the electrode layer. The benefit agent delivery system may further comprise a voltage source that is coupled to the conductive layer and the electrode layer. When a voltage is applied from the voltage source coupled to the conductive layer and the electrode layer, the resulting electric current may flow through the medium. When a voltage is applied from a voltage source coupled to the conductive layer and the electrode layer, the metallic material is removed from the sealing layer, creating a porous sealing layer. The electrode layer may be porous.

In one embodiment, the polymeric material of the sealing layer may comprise an acrylate, a methacrylate, a polycarbonate, a polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polyurethane, alginate, and polystyrene. The metallic material of the sealing layer may be metal particles, metal wires, metal fibers, metal flakes, metal rods, metal aggregates, or metal disks. The smallest dimension of the metal particles, metal wires, metal fibers, metal rods, and metal aggregates may be from about 1 µm to about 100 µm. The metal flakes and metal disks may have average thickness of from about 1 nm to about 200 nm, and average diameter of from 100 nm to about 500 µm. The metallic material of the sealing layer may also be metal nanoparticles, metal nanowires, metal nanofibers or combinations thereof. The smallest dimension of the metal nanoparticles, metal nanowires, and metal nanofibers may be from about 20 nm to about 1 µm. The metallic material of the sealing layer may comprise metal elements such as silver, copper, platinum, gold, zinc, nickel, chromium or combinations thereof.

In one embodiment, the microcells may comprise a variety of benefit agents. The benefit agent may be a pharmaceutical agent, a vaccine, an antibody, a hormone, a protein, a nucleic acid, a nutraceutical agent, a nutrient, a cosmetic agent, a fragrance, a malodor removing agent, an agricultural agent, an air care agent, a preservative, an antimicrobial agent and other benefit agents.

In one embodiment, the benefit agent may be dissolved or dispersed in the carrier. The carrier may be water, an organic compound, a silicone compound, or combinations thereof. The organic compound may be an alcohol, an ester, an amide, an ether, a carboxylic acid, a hydrocarbon or other organic compound. The organic compound may be an organic solvent, such as DMSO, ethylene glycol, polyethylene glycol, propylene glycol, dipropylene glycol, glycerin, octane, nonane, triethyl citrate, ethylene carbonate, or dimethyl carbonate.

The medium that is included in the plurality of microcells may comprise more than 0.01 weight %, or more than 0.1 weight %, or more than 1 weight % of the benefit agent by weight of the medium. The medium may comprise from 0.001 weight % to 99.99 weight %, or from 0.01 weight % to 99 weight %, or from 0.1 weight % to 95 weight %, or form 5 weight % to 60 weight % of the benefit agent by weight of the medium.

In another embodiment of the benefit agent delivery system, a microcell may contain a benefit agent or a mixture of benefit agents. Because the invention includes a plurality of microcells, it is possible to have different microcells within the same benefit delivery system containing different combination of benefit agents or similar combinations having different concentrations. For example, a system may include first microcells containing a first benefit agent and second microcells containing a second benefit agent, or a system may include first microcells containing a benefit agent at a first concentration and second microcells containing the same benefit agent at a second concentration. In other embodiments, the system may include first microcells containing a benefit agent and second microcells containing an adjuvant. Other combinations of benefit agents, additives, and concentrations will be evident to one of skill in the art.

In another aspect, the invention is a method of operation a benefit agent delivery system comprising the steps of (1) providing a benefit agent delivery system comprising (a) a conductive layer, (b) a microcell layer comprising a plurality of microcells, wherein each microcell includes an opening and contains a carrier and a benefit agent, (c) a sealing layer spanning the opening of each microcell and comprising a polymeric material and a metallic material, (d) an electrode layer; and (e) a voltage source; the conductive layer, the microcell layer, the sealing layer and the electrode layer are vertically stacked upon each other; the microcell layer and the sealing layer are disposed between the conductive layer and the electrode layer; the voltage source is coupled to the conductive layer and the electrode layer; (2) applying a voltage potential difference between the conductive layer and the electrode layer to generate an electric field having a polarity causing the migration of the metallic material onto a surface of the microcell adjacent to the conductive layer. When the voltage is applied, the resulting electric current flows through the medium. The rate of delivery of the benefit agent may be controlled by the selection of the applied voltage potential

BRIEF DESCRIPTION OF DRAWINGS

In FIGS. 6C and 6D a combination of top and bottom exposure is used, allowing the walls in one lateral direction to be cured by top photomask exposure, and the walls in another lateral direction to be cured bottom exposure through the opaque base conductor film. This process allows microcell walls to be prepared with varying porosity for use with lateral motion embodiments;

In FIG. 9 a switch is coupled to a wireless receiver allowing a user to activate a microcell to trigger the delivery of the benefit agent with an application on a mobile phone or other wireless device;

In FIG. 10, a plurality of electrodes is coupled to a matrix driver that is coupled to a wireless receiver, thereby allowing an application to activate the delivery of the desired benefit agent;

DETAILED DESCRIPTION OF THE INVENTION

Figure 1A:
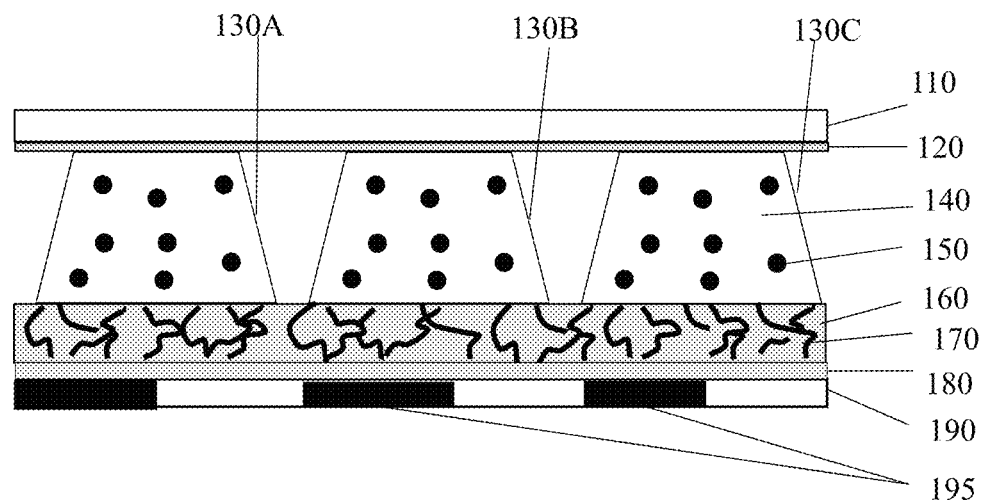
FIG. 1A illustrates an embodiment of a benefit agent delivery system including a conductive layer, a plurality of microcells comprising a benefit agent, a sealing layer with a metallic material, and an electrode layer.

The invention provides a benefit agent delivery system whereby benefit agents can be released on demand and/or a variety of different benefit agents can be delivered from the same system and/or different concentrations of benefit agents can be delivered from the same system. The invention can be used to deliver a pharmaceutical agent, a vaccine, an antibody, a hormone, a protein, a nucleic acid, a nutrient, a nutraceutical agent, a cosmetic agent, a fragrance, a malodor removing agent, an air care agent, an agricultural agent, an air care agent, an anti-microbial agent, a preservative, and other benefit agents. Pharmaceutical agents and cosmetic agents may be delivered to patients transdermally. However, the invention may be used to deliver benefit agents to animals, generally. For example, the invention can deliver tranquilizing agents to a horse during transport. In addition, the invention may be used to deliver benefit agents to other surfaces or spaces.

"Adhesive layer" of the benefit agent delivery system is a layer that establishes an adhesive connection between two other layers of the system. An adhesive layer may have thickness of from 200 nm to 5 mm, or from 1 µm to 100 µm.

"Porous diffusion layer" is a layer of the benefit agent delivery system that has average pore size that is larger than 0.2 nm. "Rate control layer" is a layer of the benefit agent delivery system that has average pore size that is 0.2 nm or smaller.

In one embodiment of the present invention, the benefit agent delivery system includes a conductive layer, a microcell layer, a sealing layer, and an electrode layer. The conductive layer, the microcell layer, the sealing layer, and the electrode layer are vertically stacked upon each other. In a preferred embodiment, the conductive layer, the microcell layer, the sealing layer, and the electrode layer are vertically stacked upon each other in this order. The benefit agent delivery system may also comprise a voltage source connecting the conductive layer with the electrode layer.

The microcell layer comprises a plurality of microcells containing a medium. Each of the plurality of microcells may have a volume greater than 0.01 nL, greater than 0.05 nL, greater than 0.1 nL, greater than 1 nL, greater than 10 nL, or greater than 100 nL. The medium, which is a benefit agent formulation, comprises a carrier and a benefit agent. The medium may comprise more than 0.01 weight %, or more than 0.1 weight %, or more than 1 weight % of the benefit agent by weight of the medium. The medium may comprise from 0.001 weight % to 99.99 weight %, or from 0.01 weight % to 99 weight %, or from 0.1 weight % to 95 weight %, or form 5 weight % to 60 weight % of the benefit agent by weight of the medium.

The carrier may be a liquid, a semi-solid, a gel, such as a hydrogel, or combinations thereof. The carrier may comprise water, an organic compound, a silicone compound or combinations thereof. The organic compound may be an alcohol, an ester, an amide, an ether, a carboxylic acid, a hydrocarbon and other organic compounds. The organic compound may be an organic solvent such as DMSO, ethylene glycol, polyethylene glycol, propylene glycol, dipropylene glycol, glycerin, octane, nonane, triethyl citrate, ethylene carbonate, dimethyl carbonate and other organic solvents. The organic compound may be a biocompatible non-polar liquid. The organic compound may be a natural oil, such as vegetable oil, fruit oil, or nut oil. The silicone compound may be a silicone oil. In other embodiments, the carrier may be an aqueous liquid, such as water or an aqueous buffer. The content of carrier in the medium may be from about 1 weight % to about 99 weight %, preferably from about 5 weight % to about 95 weight %, more preferably from about 10 weight % to about 90 weight % by weight of the medium. The medium may also comprise a polymeric material. In one example, a benefit agent may be dispersed in the polymeric material before it is added into the microcells.

The medium may also comprise additives, such as charge control agents, rheology modifiers, and chelants. A charge control agent is typically a molecule comprising ionic or other polar groups, such as, for example, positive or negative ionic groups, which are preferably attached to a non-polar chain (typically a hydrocarbon chain). Rheology modifiers are compounds, typically polymeric materials, which adjust the viscosity of the medium to the desired value. A chelant is a compound, which is able to chelate metal cations. The presence of the chelant may facilitate the migration of the metallic material from the sealing layer. Non-limiting example of chelants include ethylenediaminetetraacetic acid (EDTA), ethylene diamine di succinic acid (EDDS), aminotri(methylenephosphonic acid) (ATMP), 1,3-diamino-2-propanoltetraacetic acid (DTPA), dipicolinic acid (DPA), and ethylenediamine-N,N'-bis(2-hydroxyphenylacetic acid) (EDDHA). The medium may contain from 0.001 weight % to 5 weight or from 0.01 weight % to 3 weight or from 0.1 weight to 1 weight % of a chelant by weight of the medium.

The microcells include an opening. The largest dimension of the microcell opening may be from 30 µm to 300 µm, or from 30 µm to 180 µm, or from about 80 µm to 150 µm. A sealing layer spans the opening of each microcell. The sealing layer comprises a polymeric material and a metallic material. The metallic material may comprise metal particles, metal wires, metal fibers, metal flakes, metal rods, metal aggregates, metal disks, and combinations thereof. The metallic material may comprise metal nanoparticles, metal nanowires, metal nanofibers, and combinations thereof. The metallic material may be present in the sealing layer as a metal-coated silica particles, metal-coated semiconductor particles, metal-coated glass beads, or metal-coated plastic beads. The metallic material of the sealing layer may comprise metal elements such as silver, copper, platinum, gold, zinc, nickel, chromium or combinations thereof. The sealing layer may also comprise a conductive material such as carbon black, carbon nanotubes, graphene or a conductive polymer. The smallest dimension of the metallic material may be from 1 nm to 1 mm, or from 20 nm to 500 µm, or from 30 nm to 100 µm. In the cases of metal wires, metal fibers, metal rods, and metal aggregates, the smallest dimension may be from 1 µm to 100 µm, or from 2 µm to 50 µm, or from 5 µm to 20 µm. The metal flakes and metal disks may have average thickness of from 1 nm to 200 nm, or from 5 nm to 100 nm, and average diameter of from 100 nm to 500 nm, or from 150 nm to 300 nm. The metallic material of the sealing layer may be in the form of metal nanoparticles, metal nanowires, and metal nanofibers. In these cases, the smallest dimension of the nanostructures may be from 20 nm to 1 µm, or from 50 nm to 500 nm, or from 75 nm to 250 nm. The content of the metallic material may be from about 1 weight % to about 90 weight %, preferably from about 3 weight % to about 70 weight %, more preferably from about 5 weight % to about 40 weight % by weight of the not activated sealing layer. The sealing layer may have thickness of from 500 nm to 3 mm, or from 1 µm to 100 µm.

The plurality of the microcells and the sealing layer are disposed between the conductive layer and the electrode layer. The electrode layer may comprise a single electrode. The electrode layer may be a mesh from a metallic material having rows and columns. The electrode layer may also comprise a plurality of electrodes (also called pixel electrodes), which may be independently addressed. The average largest dimension of the pixel electrodes may be from about 4 µm to about 4 mm, preferably from about 10 µm to about 500 µm, more preferably from about 50 to about 200

μm. The electrode layer may also comprise a continuous conductive material. The continuous conductive material may be a pre-formed conductor film, such as indium tin oxide (ITO) conductor lines. Other conductive materials, such as silver or aluminum, may also be used. The thickness of the electrode layer may be from 500 nm to 5 mm, or from 1 μm to 500 μm. In the case of the continuous conductive material, such as ITO, the thickness of the electrode layer may be from 0.1 nm to 1 μm, or from 1 nm to 100 nm. The electrode layer may be porous, having average pore size larger than 0.2 nm, or larger than 10 nm, or larger than 100 nm, or larger than 1 μm, or larger than 10 μm, or larger than 100 μm. The electrode layer may also have average pore size less than 0.2 nm. In general, the smaller the average pore size, the lower the rate of delivery of the benefit agent from the delivery system.

The conductive layer may comprise a continuous conductive material. The continuous conductive material may be a pre-formed conductor film, such as indium tin oxide (ITO) conductor lines. Other conductive materials, such as silver or aluminum, may also be used. In this case, the thickness of the electrode layer may be from 0.1 nm to 1 μm, or from 1 nm to 100 nm. The conductive layer may also comprise a mesh of a metallic material having rows and columns. It may also comprise a plurality of electrodes, such as pixel electrodes, which may be independently addressed. In these cases, the thickness of the conductive layer may be from 500 nm to 5 mm, or from 1 μm to 500 μm.

Figure 1B:
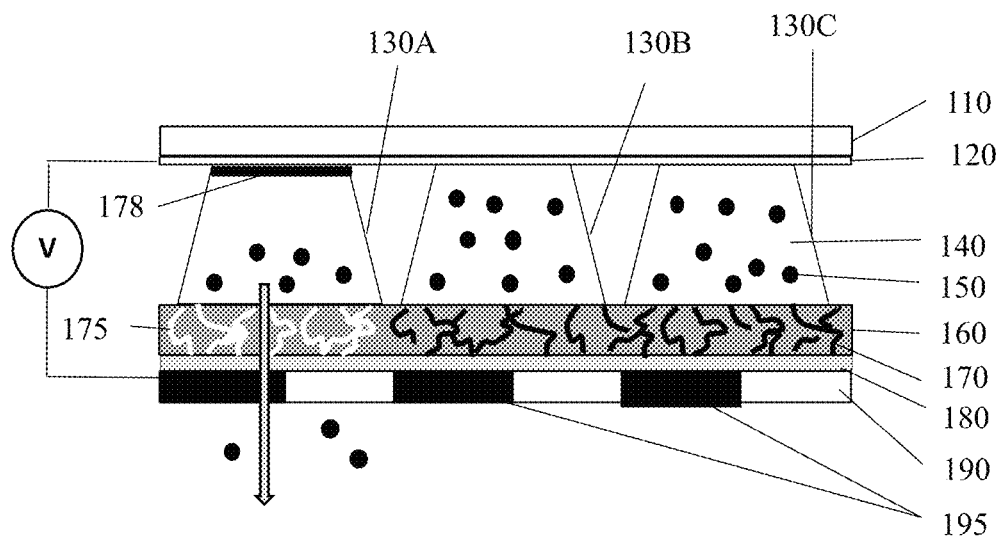
FIG. 1B illustrates an embodiment of a benefit agent delivery system including a continuous conductive layer, a plurality of microcells comprising a benefit agent, a porous sealing layer, and a voltage source. In the system depicted in FIG. 1B, the benefit agent may pass through the porous sealing layer of one of the microcells to be delivered where desired.

The benefit agent delivery system comprises a plurality of microcells having a sealing layer that is initially impermeable (or has low permeability) to the benefit agent as depicted in FIG. 1A. Upon application of a voltage between the conductive layer and an electrode of the electrode layer, the metallic material of the sealing layer is removed from the sealing layer. It may migrate through the microcell and deposited onto the inside surface of the microcell adjacent to the conductive layer. The applied voltage may be from about 1 to about 240 V, preferably from about 5 to about 130 V, more preferably from about 20 to about 80 V. The duration of the application of the voltage may be from about 1 second to about 120 minute, preferably from about 10 seconds to about 60 minutes, more preferably from about 1 minute to about 30 minutes. When a voltage is applied from a voltage source between the conductive layer and the electrode layer, the resulting electric current may flow through the medium. It is likely that the metallic material of the sealing layer is oxidized to the corresponding metal salt near the anode with the application of the electric field. The metal salt may be dissolved into the medium in the microcell and then it may be reduced near the cathode into its metal form and deposited on the inside surface of the microcell adjacent to the conductive layer. The process creates porosity in the sealing layer as depicted in FIG. 1B, activating the microcell. As a result, the benefit agent of the microcell may exit the corresponding microcell from the surface adjacent to the sealing layer, as the arrow of FIG. 1B shows, to be delivered on the desired surface or space. The porosity of the sealing layer of the activated microcell may be from about 0.01% to about 80%, preferably from about 0.5% to about 50%, more preferably from about 1% to about 20% determined as total volume of pores per total volume of the corresponding sealing layer. The polarity of the voltage that triggers the migration of the metal and the activation of the microcell is such that the electrode of the electrode layer has a positive potential (anode). The ability to create porosity in the sealing layer by the application of a voltage enables the delivery of the benefit agent on demand. Because the benefit agent delivery system may comprise a plurality of microcells that can be independently activated on demand, the system has the flexibility of delivering variable quantities of benefit agents at different times. Additionally, the microcell arrays may be loaded with different benefit agents, thereby providing a mechanism to deliver different or complimentary benefit agents on demand.

In addition to more conventional applications, such as transdermal delivery of pharmaceutical compounds, the benefit agent delivery system may be the basis for delivering agricultural nutrients. The microcell arrays can be fabricated in large sheets that can be used in conjunction with hydroponic growing systems, or they can be integrated into hydrogel film farming, such as demonstrated by Mebiol, Inc. (Kanagawa, Japan). The benefit agent delivery system can be incorporated into the structural walls of smart packing, as well. The delivery system, for example, makes it possible to have long-term release of antioxidants into a package containing fresh vegetables or other items. Such packaging could dramatically improve the shelf life of certain foods and other items yet will only require the amount of antioxidant necessary to maintain freshness until the package is opened.

An overview of a benefit agent delivery system is shown in FIG. 1A. The system includes a microcell layer comprising a plurality of microcells (130A, 130B, 130C), each microcell including a medium (a benefit agent formulation), that comprises a carrier 140 and a benefit agent 150. Even if FIG. 1A (and also FIGS. 1B, 2, 3, 7, 8, 9, 10, 11, and 12) represents the benefit agent 150 as a separate macroscopic entity, which may imply a different phase than the carrier, this representation should be assumed to include the option of the benefit agent existing in a molecular state in the form of solution in the carrier or in any other form, wherein the presence of the benefit agent is not apparently visible as a separate phase. Such examples include microemulsions, nanoemulsions, colloidal dispersions, etc. Each microcell is part of an array that is formed from a polymer matrix, which is described in more detail below. The benefit agent delivery system will typically include a backing layer 110 to provide structural support and protection against moisture ingress and physical interactions. The backing layer may have thickness of from 1 μm to 5 mm, or from 25 μm to 300 μm. A portion of the microcells will have an opening that is spanned by a sealing layer 160. The sealing layer may be constructed from a variety of natural or non-natural polymers, such as comprises acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polystyrene, polyurethane or alginate. The sealing layer also comprises a metallic material in the form of metal particles, metal wires, metal fibers, metal flakes, metal rods, metal aggregates, metal disks, or combinations thereof. The sealing layer may comprise metallic material in the form of nanoparticles, metal nanowires or metal nanofibers (170). The sealing layer may also comprise additional conductive materials such as carbon black, carbon nanotubes, graphene or a conductive polymer. Non-limiting examples of conductive polymers that can be used in the sealing layer include PEDOT-PSS, polyacetylene, polyphenylene sulfide, polyphenylene vinylene, or combinations thereof. The sealing layer may also comprise a benefit agent, which is the same or different that a benefit agent included in the medium of the microcells. The benefit agent may be incorporated in the sealing layer when the sealing layer composition is prepared and before the sealing layer is used during the preparation of the benefit agent delivery system. The horizontal cross section of the microcells may have different shapes, for example, square, round, or polygonal, such as a honeycomb structure.

The plurality of microcells (130A, 130B, 130C) and the sealing layer 160 are disposed between a conductive layer 120 and an electrode layer 190. The electrode layer 190 may be a mesh from a metallic material having rows and columns. The electrode layer may also comprise or a plurality of electrodes. The electrode layer may comprise a plurality of electrodes 195. Often the system will additionally include an adhesive layer 180. The electrode layer and the sealing layer may be integrated into one layer. In FIG. 1A, the adhesive layer is between the sealing layer and the electrode layer. The adhesive layer and the electrode layer may be porous to the benefit agent. The adhesive layer may have thickness of from 200 nm to 5 mm, or from 1 μm to 100 μm.

FIG. 1B shows an example of a benefit agent delivery system after the activation of a microcell. As described above, the activation takes place via the application of a voltage 210 across the microcell, leading to the migration of the metallic material 170. The migration of the metallic material 170 creates a layer having open channels 175. Thus, the sealing layer adjacent to the activated microcell become porous. More specifically, in FIG. 1B the sealing layer portion that spans the opening of the leftmost microcell 130A is porous, because the initially present metallic material 170 has migrated, creating open channels 175. This migration results in the deposition of the metallic material 170 on the surface of microcell 130A adjacent to the conductive layer 120. As shown in FIG. 1B, the benefit agent that is present in microcell 130A, may exit the microcell through the now porous sealing layer (as the arrow indicates) and can be delivered on a desired surface or space. The rate of delivery of the benefit agent can be controlled by a variety of ways. Examples include the content of the metallic material in the sealing layer and the size of the smallest dimension of the metallic material, which is dispersed in the sealing layer. These parameters affect the porosity of the sealing layer. Typically, the larger the content of the metallic material in the sealing layer and the larger the smallest dimension of the metal material is, the more porous the sealing layer will be and the higher the rate of delivery. Other parameters that may affect the rate of delivery include the nature of the benefit agent and the carrier and the concentration of the benefit agent in the carrier composition. The inclusion of a rate control layer in the benefit agent delivery system may also control the rate of delivery, as described in more detail below. The benefit agent may be present in the microcell in a molecular form, that is, as a solution in the carrier and/or as an entity in a different phase as a dispersion or an emulsion. In the latter case (different phase), the particle or droplet size of the dispersion or emulsion will also affect the rate of delivery. The duration of the delivery of the benefit agent can be also controlled by the magnitude of the applied voltage, which will affect the rate of the migration of the metallic material of the sealing layer and the rate of the creation of the porosity in the sealing layer. Application of higher voltage typically results in higher rate of delivery of the benefit agent. The useful physical form of the benefit agent may be gaseous, independently of the actual physical form exiting the benefit agent delivery system. For example, fragrance molecules vaporize to reach the nasal odor sensors of the user before they are detected. Thus, this kind of benefit agents may exit the delivery system as a liquid or as a gas.

Figure 3A:
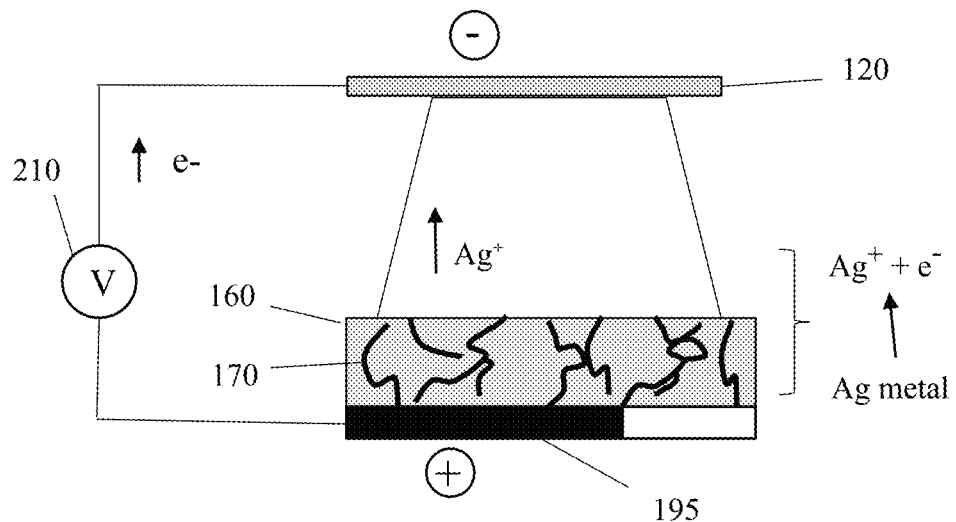
FIGS. 3A and 3B illustrates a potential mechanism for the migration the metallic material of the sealing layer.
Figure 3B:
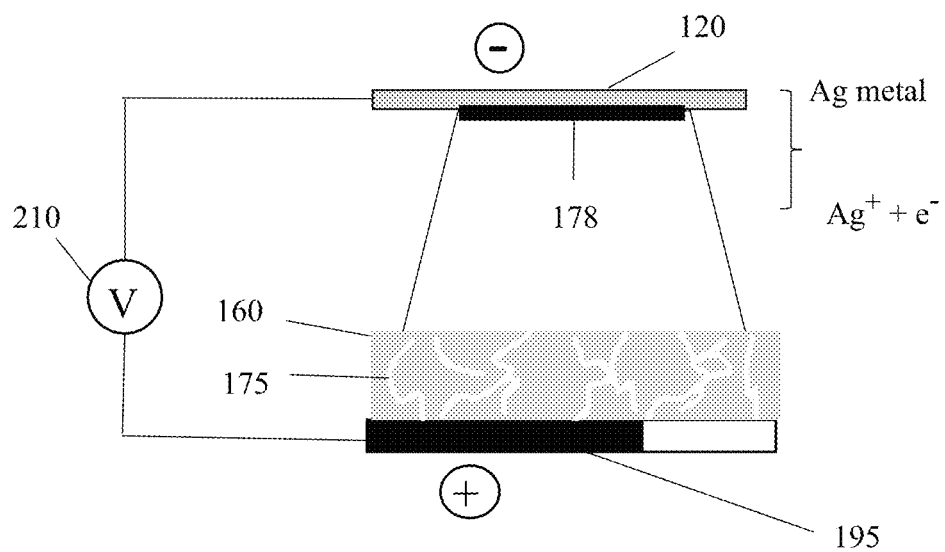

The activation of a microcell is achieved by an applied voltage between the conductive layer 120 and the corresponding electrode 195, as illustrated in FIGS. 3A and 3B. The application of the voltage results in an electric current, which flows through the medium of the microcell. In the embodiment illustrated in FIGS. 3A and 3B, the sealing layer 160 of the microcell comprises a polymeric material wherein silver nanofibers 170 are dispersed, as illustrated in FIG. 3A. The applied voltage 210 is such that the electrode 195 has positive polarity. The silver nanofibers of the sealing layer migrate and are redeposited onto the inside surface of the microcell (178). It is likely that this is the results of oxidization of the silver nanofibers to silver salts comprising silver cation (Ag+), which may dissolve in the medium of the microcell and may move towards the conductive layer 120. The electrons generated from the metallic material oxidation may also move towards the conductive layer 120 via the electrical coupling between the conductive layer 120 and the electrode 195. In FIG. 3B, the result of this process is illustrated. The silver cations may be reduced to silver metal on the inside surface of the microcell adjacent to the conductive layer by the transferred electrons. The metallic silver is then deposited on the inside surface of the microcell (178). The migration of the silver nanofibers 170 from the sealing layer creates open channels 175 on the sealing layer 160, activating the microcell and enabling the delivery of the benefit agent, which is present in the microcell.

Figure 4:
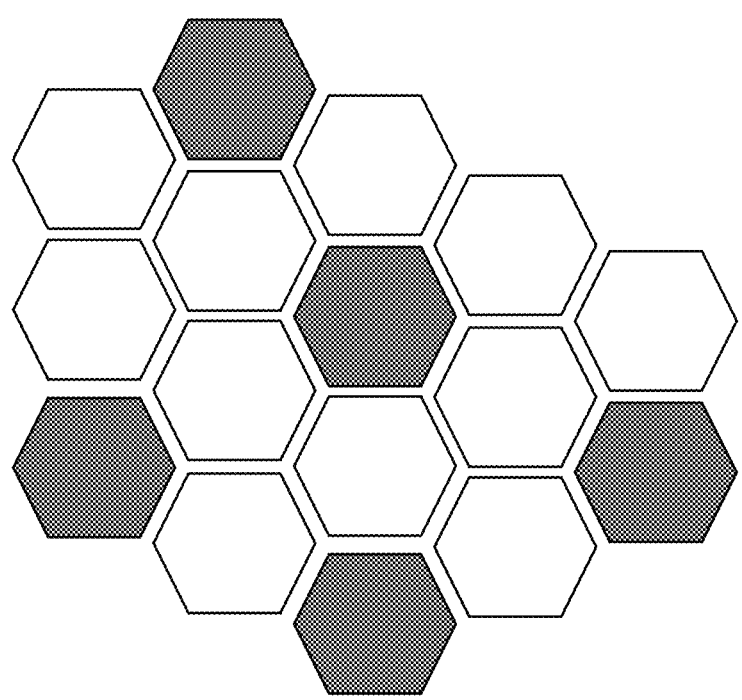
FIG. 4 illustrates a benefit agent delivery system including a plurality of different types of benefit agents and/or a plurality of concentrations of benefit agents in the same delivery system.

In addition to regulating the rate of delivery of benefit agent, the microcell construction of the invention lends itself to making arrays of differing benefit agents, or arrays of different concentrations, as illustrated in FIG. 4. Because the microcells can be individually activated with an active matrix of electrodes, it is possible to provide varying benefit agents on demand and to produce complex dosing profiles. Using injection with inkjet or other fluidic systems, individual microcells can be filled to enable a variety of different benefit agents to be included in a benefit agent delivery system. For example, a system of the invention may include nicotine at four different concentrations, thereby allowing different dosages to be delivered at different times during the day. For example, shortly after waking up the most concentrated dose may be delivered (dark gray), followed by a much lower taper dose during the day (speckled), until the time that a user needs another more concentrated dose. It is possible to include different benefit agents in the same microcell. For example, the system illustrated in FIG. 4 may also include an analgesic (stripes) to reduce swelling and itching in the area of the skin that is in contact with the delivery system. Of course, a variety of combinations are possible, and varying microcells might include pharmaceuticals, nutraceuticals, nutrients, adjuvants, vitamins, vaccines, hormones, cosmetic agents, fragrances, preservatives, etc. Furthermore, the arrangement of the microcells may not be distributed. Rather, the microcells may be filled in clusters, which makes filling and activation more straightforward. In other embodiments, smaller microcell arrays may be filled with the same medium, i.e., having the same benefit agent at the same concentration, and then the smaller arrays assembled into a larger array to make a delivery system of the invention.

Figure 2:
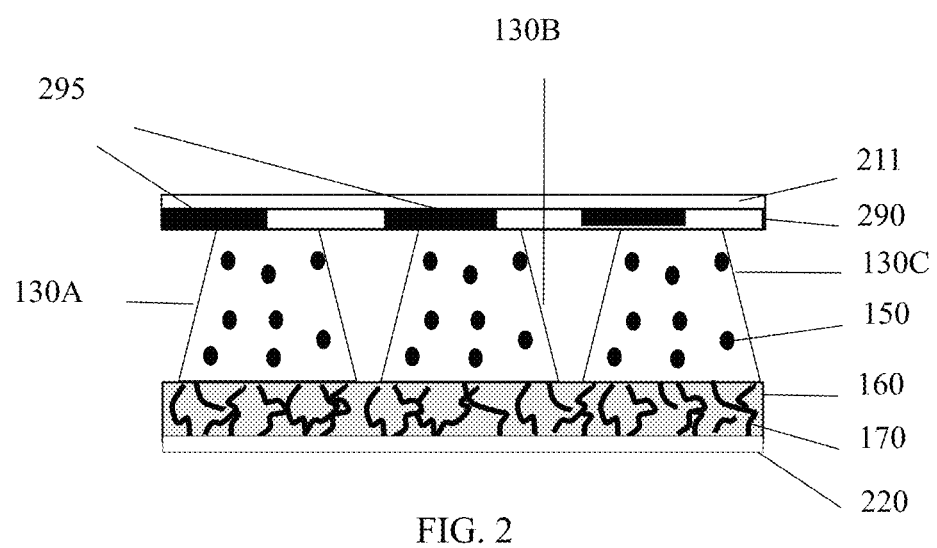
FIG. 2 illustrates another embodiment of a benefit agent delivery system including an conductive layer, a plurality of microcells comprising a benefit agent, a sealing layer with a metallic material, and a continuous electrode layer.

In another embodiment illustrated by FIG. 2, the benefit agent delivery system includes a conductive layer 290, a microcell layer comprising a plurality of electrodes (130A 130B, 130C), a sealing layer 160 comprising a metallic material 170, and an electrode layer 220. The conductive layer 290, the microcell layer, the sealing layer 160, and the electrode layer 220 are vertically stacked upon each other. In this embodiment, the conductive layer 290 may comprises multiple electrodes 295 (such as pixel electrodes), or it may comprise a mesh from a metallic material having rows and columns. The benefit agent delivery system may also comprise a backing layer 211 as well as a voltage source that connects the electrode layer with the porous conductive layer (not shown in FIG. 2). The plurality of microcells comprise a benefit agent 150. In this embodiment, the electrode layer may be a continuous conductive material (such as ITO). The electrode layer and the sealing layer may be integrated in one layer.

Figure 5:
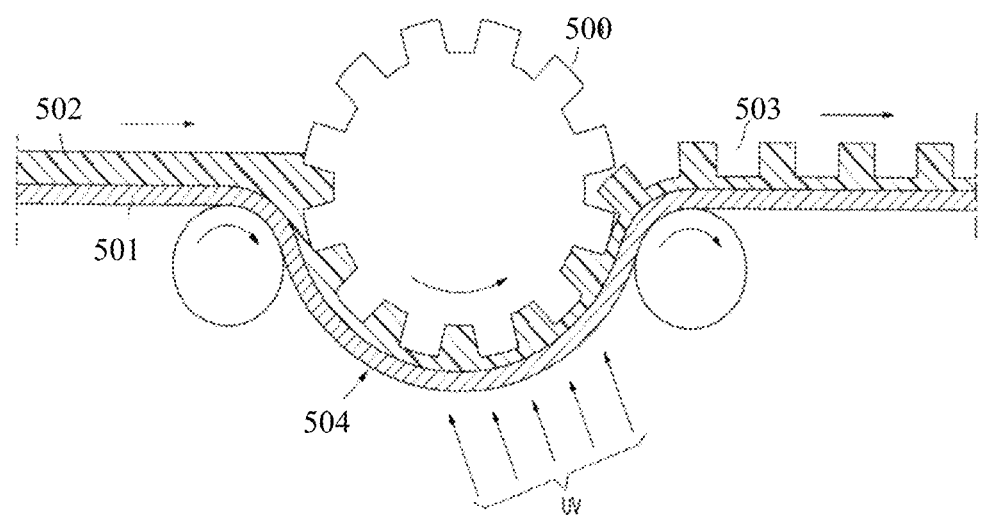
FIG. 5 shows a method for making microcells for the invention using a roll-to-roll process.

Techniques for constructing microcells. Microcells may be formed either in a batchwise process or in a continuous roll-to-roll process as disclosed in U.S. Pat. No. 6,933,098. The latter offers a continuous, low cost, high throughput manufacturing technology for production of compartments for use in a variety of applications including benefit agent delivery and electrophoretic displays. Microcell arrays suitable for use with the invention can be created with microembossing, as illustrated in FIG. 5. A male mold 500 may be placed either above the web 504 or below the web 504 (not shown); however, alternative arrangements are possible. For examples, please see U.S. Pat. No. 7,715,088, which is incorporated herein by reference in its entirety. A conductive substrate may be constructed by forming a conductor film 501 on polymer substrate that becomes the backing for a device. A composition comprising a thermoplastic, thermoset, or a precursor thereof 502 is then coated on the conductor film. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A cross-linkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about −70° C. to about 150° C., preferably from about −20° C. to about 50° C. The microembossing process is typically carried out at a temperature higher than the $T_g$. A heated male mold or a heated housing substrate against which the mold presses may be used to control the microembossing temperature and pressure.

As shown in FIG. 5, the mold is released during or after the precursor layer is hardened to reveal an array of microcells 503. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin, which should have a good release property against the mold surface.

Microcell arrays for the invention typically include a pre-formed conductor film, such as indium tin oxide (ITO) conductor lines; however, other conductive materials, such as silver or aluminum, may be used. The conductive layer may be backed by or integrated into substrates such as polyethylene terephthalate, polyethylene naphthalate, polyaramid, polyimide, polycycloolefin, polysulfone, epoxy and their composites. The conductor film may be coated with a radiation curable polymer precursor layer. The film and precursor layer are then exposed imagewise to radiation to form the microcell wall structure. Following exposure, the precursor material is removed from the unexposed areas, leaving the cured microcell walls bonded to the conductor film/support web. The imagewise exposure may be accomplished by UV or other forms of radiation through a photomask to produce an image or predetermined pattern of exposure of the radiation curable material coated on the conductor film. Although it is generally not required, the mask may be positioned and aligned with respect to the conductor film, i.e., ITO lines, so that the transparent mask portions align with the spaces between ITO lines, and the opaque mask portions align with the ITO material (intended for microcell cell floor areas).

Figure 6A:
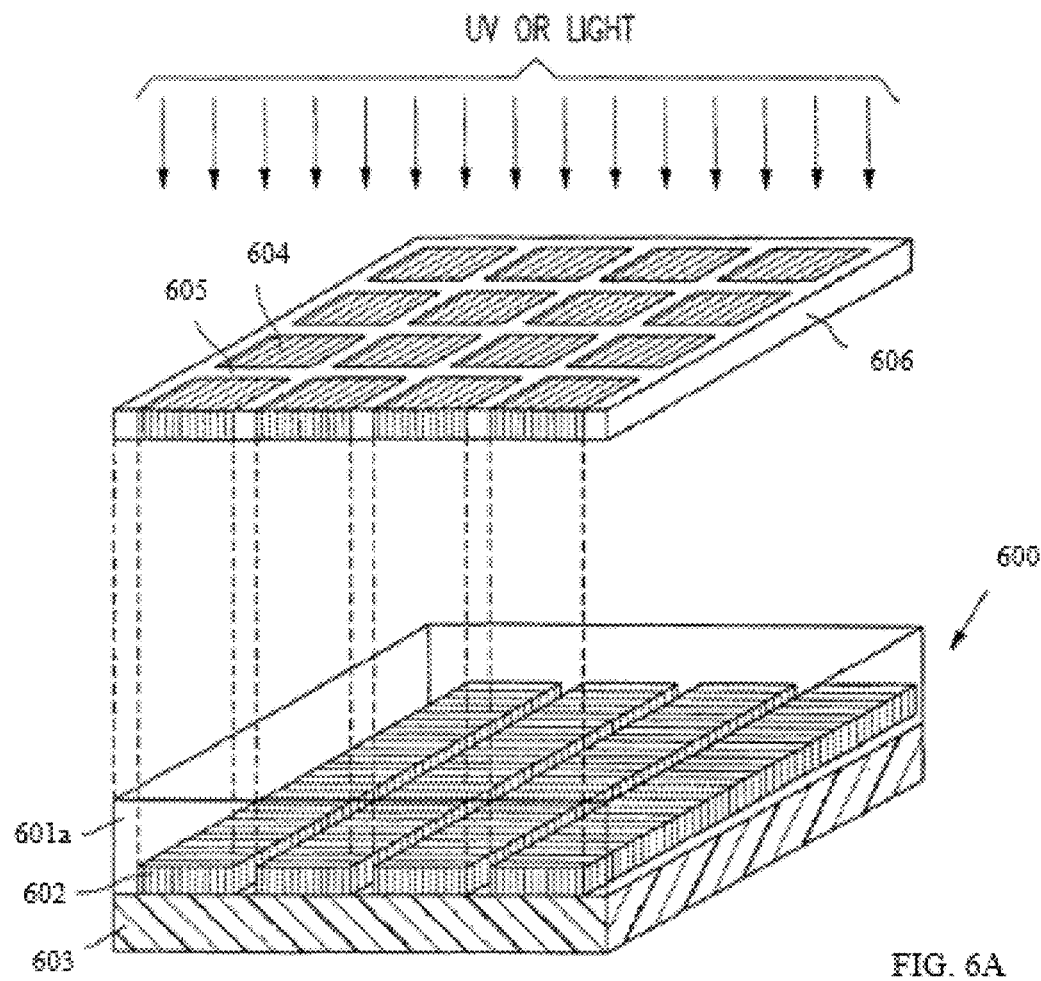
FIGS. 6A and 6B detail the production of microcells for an active molecule delivery system using photolithographic exposure through a photomask of a conductor film coated with a thermoset precursor.
Figure 6B:
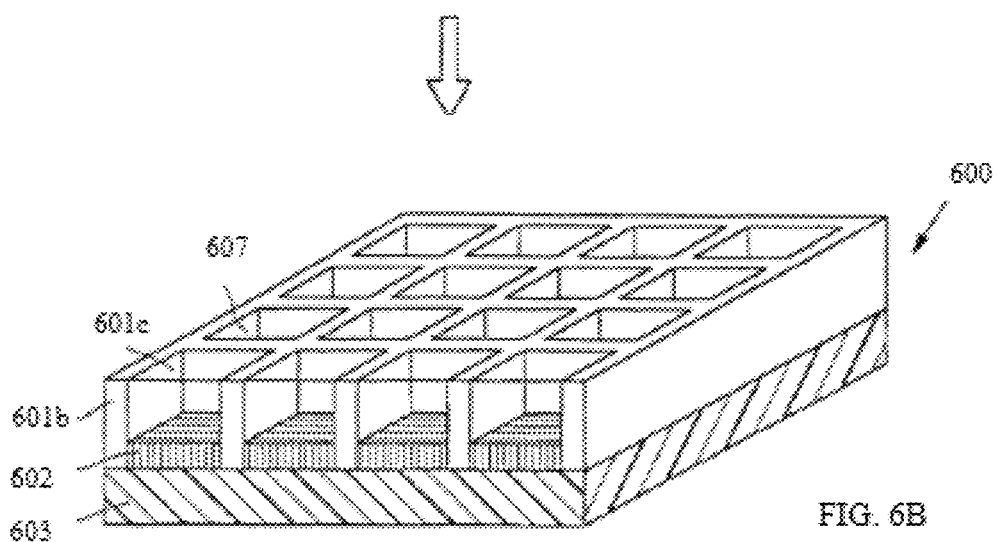

Photolithography. Microcells can also be produced using photolithography. Photolithographic processes for fabricating a microcell array are illustrated in FIGS. 6A and 5B. As shown in FIGS. 6A and 6B, the microcell array 600 may be prepared by exposure of a radiation curable material 601*a* coated by known methods onto a conductor electrode film 602 to UV light (or alternatively other forms of radiation, electron beams and the like) through a mask 606 to form walls 601b corresponding to the image projected through the mask 606. The base conductor film 602 is preferably mounted on a supportive substrate base web 603, which may comprise a plastic material.

In the photomask 606 in FIG. 6A, the dark squares 604 represent the opaque area and the space between the dark squares represents the transparent area 605 of the mask 606. The UV radiates through the transparent area 605 onto the radiation curable material 601a. The exposure is preferably performed directly onto the radiation curable material 601a, i.e., the UV does not pass through the substrate 603 or base conductor 602 (top exposure). For this reason, neither the substrate 603, nor the conductor 602, needs to be transparent to the UV or other radiation wavelengths employed.

As shown in FIG. 6B, the exposed areas 601b become hardened and the unexposed areas (protected by the opaque area 604 of the mask 606) are then removed by an appropriate solvent or developer to form the microcells 607. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

Figure 6C:
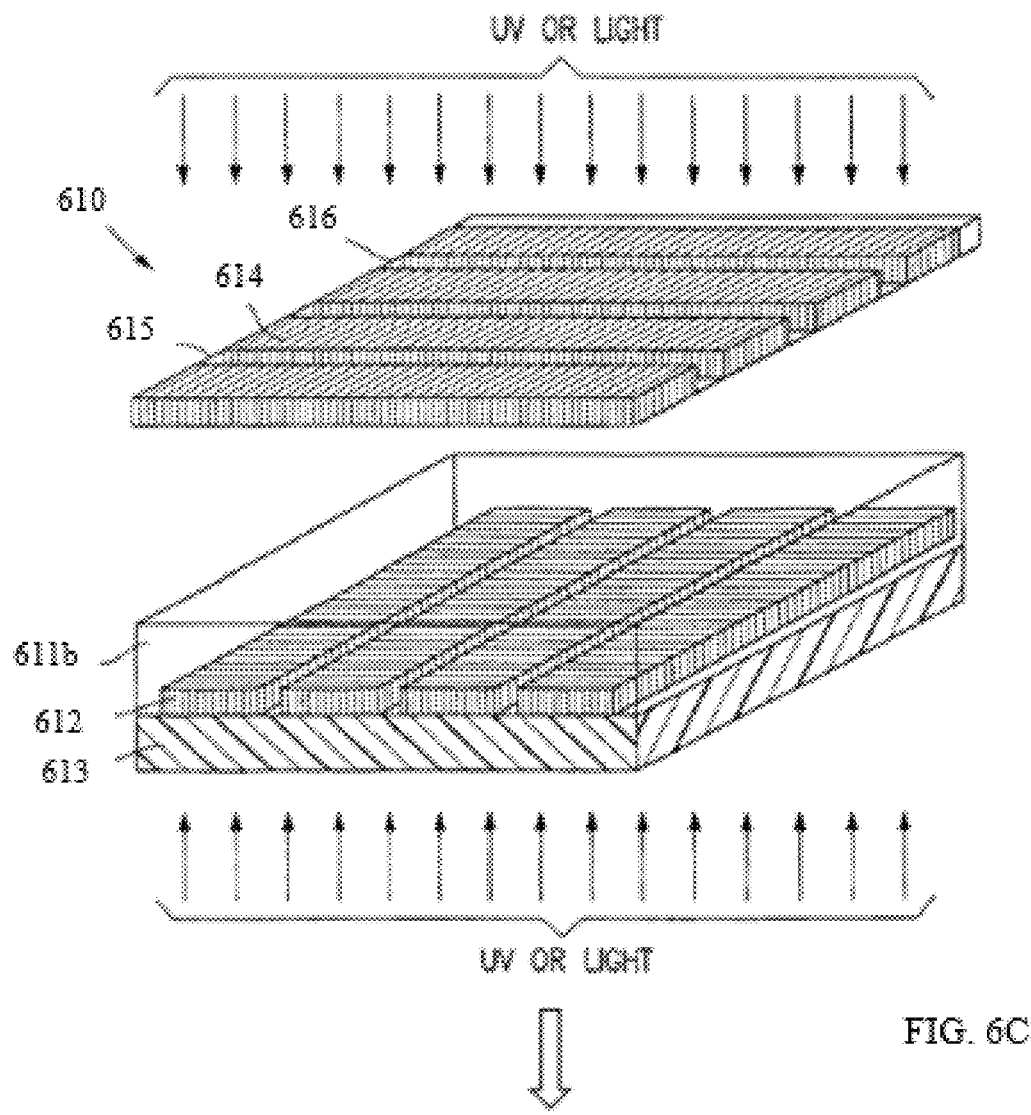
FIGS. 6C and 6D detail an alternate embodiment in which microcells for a benefit agent delivery system are fabricated using photolithography.
Figure 6D:
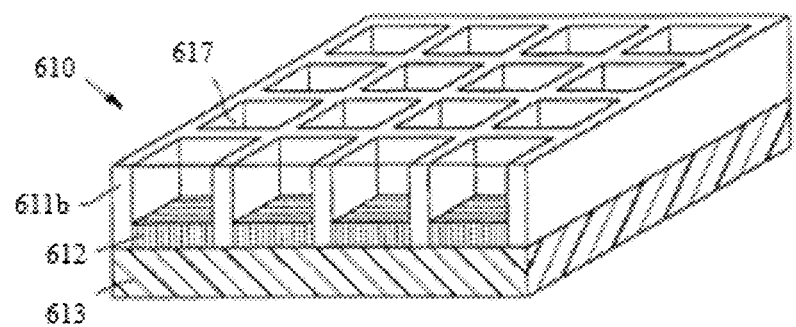

Imagewise Exposure. Still another alternative method for the preparation of the microcell array of the invention by imagewise exposure is illustrated in FIGS. 6C and 6D. When opaque conductor lines are used, the conductor lines can be used as the photomask for the exposure from the bottom. Durable microcell walls are formed by additional exposure from the top through a second photomask having opaque lines perpendicular to the conductor lines. FIG. 6C illustrates the use of both the top and bottom exposure principles to produce the microcell array 610 of the invention. The base conductor film 612 is opaque and line-patterned. The radiation curable material 611a, which is coated on the base conductor 612 and substrate 613, is exposed from the bottom through the conductor line pattern 612, which serves as the first photomask. A second exposure is performed from the "top" side through the second photomask 616 having a line pattern perpendicular to the conductor lines 612. The spaces 615 between the lines 614 are substantially transparent to the UV light. In this process, the wall material 611b is cured from the bottom up in one lateral orientation, and cured from the top down in the perpendicular direction, joining to form an integral microcell 617. As shown in FIG. 6D, the unexposed area is then removed by a solvent or developer as described above to reveal the microcells 617.

The microcells may be constructed from thermoplastic elastomers, which have good compatibility with the microcells and do not interact with the media. Examples of useful thermoplastic elastomers include ABA, and (AB)n type of di-block, tri-block, and multi-block copolymers wherein A is styrene, α-methylstyrene, ethylene, propylene or norbornene; B is butadiene, isoprene, ethylene, propylene, butylene, dimethylsiloxane or propylene sulfide; and A and B cannot be the same in the formula. The number, n, is ≥1, preferably 1-10. Particularly useful are di-block or tri-block copolymers of styrene or ox-methylstyrene such as SB (poly(styrene-b-butadiene)), SBS (poly(styrene-b-butadiene-b-styrene)), SIS (poly(styrene-b-isoprene-b-styrene)), SEBS (poly(styrene-b-ethylene/butylenes-b-stylene)) poly(styrene-b-dimethylsiloxane-b-styrene), poly((α-methylstyrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene). Commercially available styrene block copolymers such as Kraton D and G series (from Kraton Polymer, Houston, Tex.) are particularly useful. Crystalline rubbers such as poly(ethylene-co-propylene-co-5-methylene-2-norbornene) or EPDM (ethylene-propylene-diene terpolymer) rubbers such as Vistalon 6505 (from Exxon Mobil, Houston, Tex.) and their grafted copolymers have also been found very useful.

The thermoplastic elastomers may be dissolved in a solvent or solvent mixture, which is immiscible with the carrier in the microcells and exhibits a specific gravity less than that of the carrier. Low surface tension solvents are preferred for the overcoating composition because of their better wetting properties over the microcell walls and the fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkalies such as heptane, octane or Isopar solvents from Exxon Chemical Company, nonane, decane and their isomers), cycloalkanes (preferably $C_{6-12}$ cycloalkanes such as cyclohexane and decalin and the like), alkylbezenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers). Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants from OSi, Greenwich, Conn.) may also be included in the composition to improve the adhesion of the sealant to the microcells and provide a more flexible coating process. Other ingredients including cross-linking agents (e.g., bisazides such as 4,4'-diazidodiphenyl-methane and 2,6-di-(4'-azidobenzal)-4-methylcyclohexanone), vulcanizers (e.g., 2-benzothiazolyl disulfide and tetramethylthiuram disulfide), multifunctional monomers or oligomers hexanediol, diacrylates, trimethylolpropane, triacrylate, divinylbenzene, thermal initiators (e.g., dilauroryl peroxide, benzoyl peroxide) and photoinitiators (e.g., isopropyl thioxanthene (ITX), Irgacure 651 and Irgacure 369 from Ciba-Geigy) are also highly useful to enhance the physico-mechanical properties of the sealing layer by cross-linking or polymerization reactions during or after the overcoating process.

After the microcells are produced, they are filled with appropriate combinations of benefits agents and carrier. The microcell array 70 may be prepared by any of the methods described above. As shown in cross-section in FIGS. 7A-7D, the microcell walls 71 extend upward from the backing layer 73 and conductive layer 72 to form the open cells. In an embodiment, a conductive layer 72 is formed on or at the backing layer 73. While FIGS. 7A-7D show the conductive layer 72 is continuous and running above the backing layer 73, it is also possible that the conductive layer 72 is continuous and running below or within the backing layer 73 or it is interrupted by the microcell walls 71. Prior to filling, the microcell array 70 may be cleaned and sterilized to assure that the benefit agents are not compromised prior to use.

The microcells are next filled with a combination of carrier 74 and the benefit agent 75. As mentioned above, different microcells may include different benefit agents. In systems for delivering hydrophobic benefit agents, the combination may be based upon a biocompatible oil or some other biocompatible hydrophobic carrier. For example, the combination may comprise a vegetable, fruit, or nut oil. In other embodiments, silicone oils may be used. In systems for delivering hydrophilic benefit agents, the combination be based upon water, other aqueous media such as phosphate buffer or polar organic solvents. The combination need not be a liquid, however, as gels, such as hydrogels and other matrices, and semi-solid materials may be suitable to deliver the benefit agents.

The microcells may be filled using a variety of techniques. In some embodiments, where a large number of neighboring microcells are to be filled with an identical composition, blade coating may be used to fill the microcells to the depth of the microcell walls 71. In other embodiments, where a variety of different composition are to be filled in a variety of nearby microcell, inkjet-type; microinjection can be used to fill the microcells. In yet other embodiments, microneedle arrays be used to fill an array of microcells with the correct compositions. The filling may be done in a one-step or multistep process. For example, all of the cells may be partially filled with an amount of carrier. The partially filled microcells are then filled with a composition comprising the carrier and one or more benefit agents to be delivered.

Figure 7A:
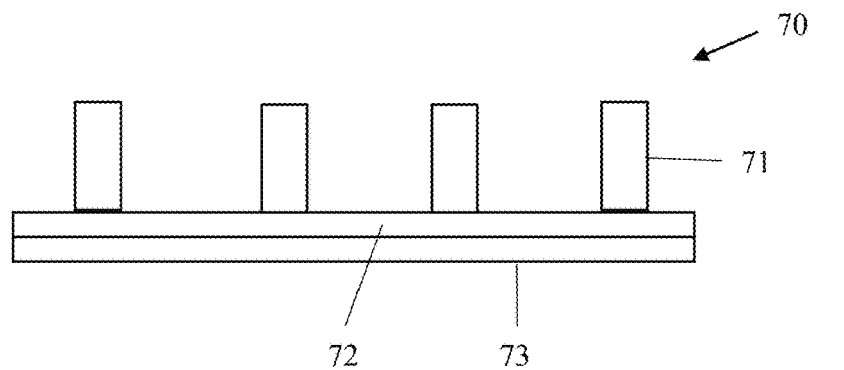
FIGS. 7A-7D illustrate the steps of filling and sealing an array of microcells to be used in a benefit agent delivery system.
Figure 7B:
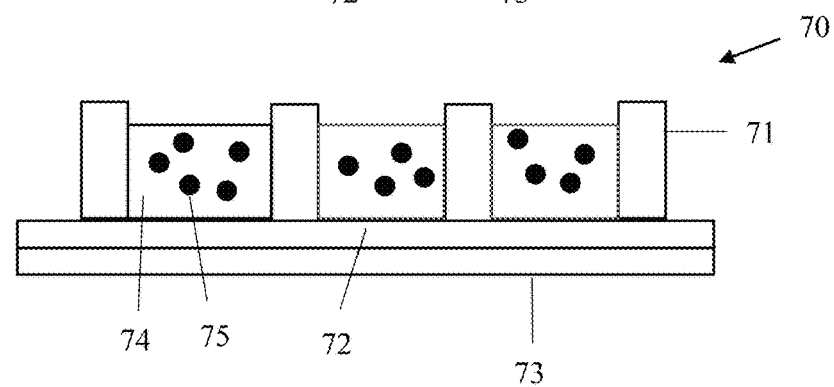
Figure 7C:
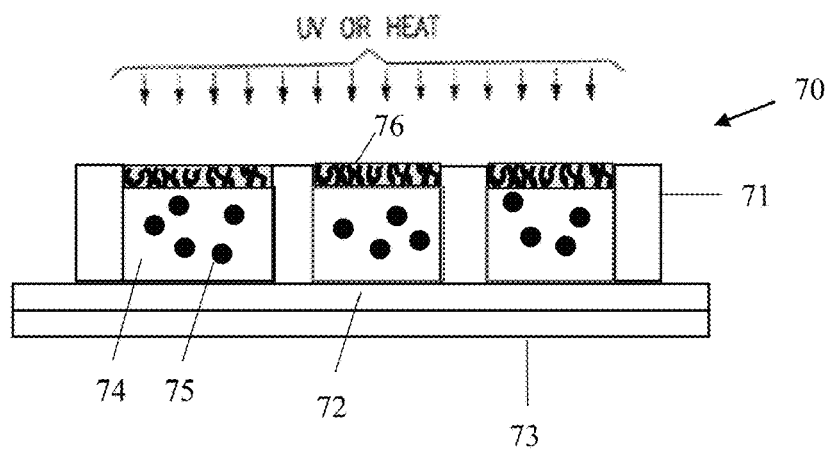
Figure 7D:
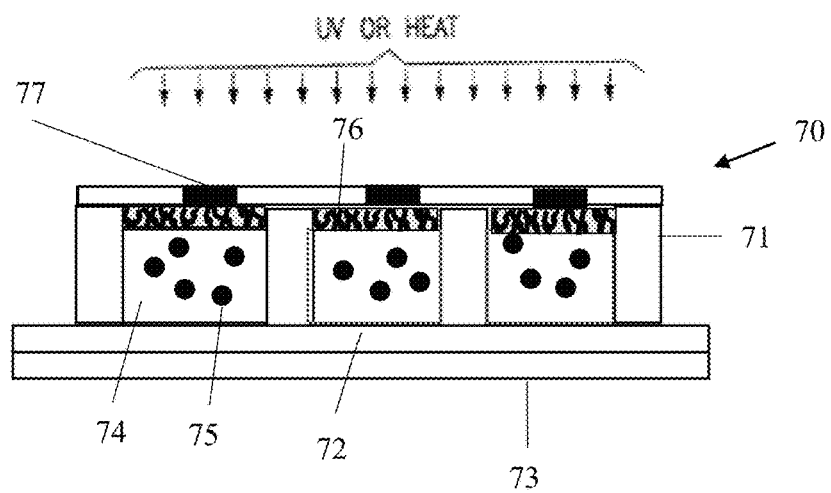

As shown in FIG. 7C, after filling, the microcells are sealed by applying a polymer composition 76 comprising metallic material, such as metal nanoparticles, metal nanowires, or metal nanofibers. In some embodiments, the sealing process may involve exposure to heat, dry hot air, or UV radiation. In most embodiments, the polymer should be insoluble or have low solubility with the carrier 74 and the benefit agent 75. The polymer composition of the sealing layer 160 can also be biocompatible and selected to adhere to the sides or tops of the microcell walls 71. An adhesive can also be used to attach the electrode layer onto the sealing layer. The adhesive may also be electrically conductive. A suitable biocompatible adhesive for sealing layer is a phenethylamine mixture, such as described in U.S. patent application Ser. No. 15/336,841, filed Oct. 30, 2016 and titled "Method for Sealing Microcell Containers with Phenethylamine Mixtures," which is incorporated herein by reference in its entirety. Accordingly, the final microcell structure is mostly impervious to leaks and able to withstand flexing without delamination or separation of the sealing layer or the electrode layer.

In alternate embodiments, a variety of individual microcells may be filled with the desired mixture by using iterative photolithography. The process typically includes coating an array of empty microcells with a layer of positively working photoresist, selectively opening a certain number of the microcells by image-wise exposing the positive photoresist, followed by developing the photoresist, filling the opened microcells with the desired mixture, and sealing the filled microcells by a sealing process. These steps may be repeated to create sealed microcells filled with other mixtures. This procedure allows for the formation of large sheets of microcells having the desired ratio of mixtures or concentrations.

After the microcells 70 are filled, the sealed array may be laminated with an electrode layer comprising a plurality of electrodes 77. The electrode layer may be porous to the benefit agents, preferably by pre-coating the electrode layer 77 with an adhesive layer, which may be a pressure sensitive adhesive, a hot melt adhesive, or a heat, moisture, or radiation curable adhesive. The laminate adhesive may be post-cured by radiation such as UV through the top conducting layer if the latter is transparent to the radiation. In other embodiments, the plurality of electrodes may be bonded directly to the sealed array of the microcell. In some embodiments, a biocompatible adhesive is then laminated to the assembly. The biocompatible adhesive will allow benefit agents to pass through while keeping the device mobile on a user. Suitable biocompatible adhesives are available from 3M (Minneapolis, MN).

Once the delivery system has been constructed, it may be covered with a release sheet to provide protection. The release sheet may also include adhesives. The benefit agent delivery system may be flexible. This means that it can be folded to a certain extend without breaking, a property similar to a thin rubber sheet. The benefit agent delivery system can be an autonomous system that can be easily transported in a small space, such as a handbag, and only needs electric power, which can be a small battery to operate.

Figure 8:
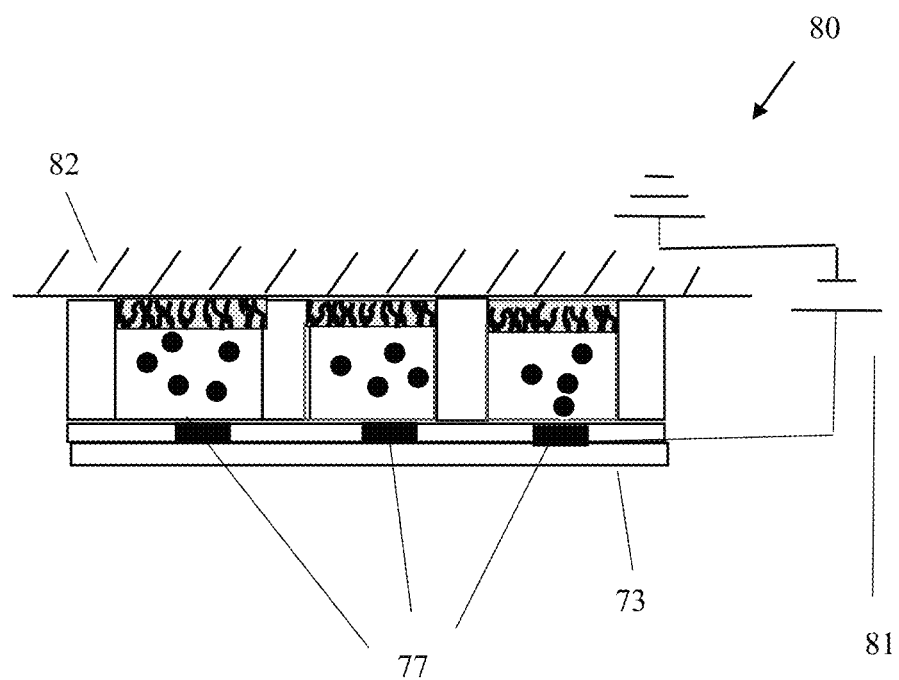
FIG. 8 illustrates an embodiment of a benefit agent delivery system including a plurality of microcells and a sealing layer comprising metallic material, which can be activated by applied electric field. The microcell is activated by an electrode while the conductivity of the skin (or other conductive substrate) provides a grounding electrode.

In some embodiments, it will not be necessary to provide a conductive layer and an electrode layer on the opposite sides of the system. For instance, as shown in FIG. 8, the benefit agent delivery system 80 may include a voltage source 81 that is grounded into the surface to which the delivery system is attached 82. This may be especially useful for transdermal delivery of drugs, where the skin's natural conductance is sufficient to provide a ground potential. Thus, the metallic material will be removed from the sealing layer. It may migrate via the medium and it may be deposited on the opposite inside surface of the microcell as a metal. This is achieved by application of a voltage to at least one of the electrodes 77 as shown in FIG. 8. It is appreciated that the electrode layer comprises a plurality of electrodes whereby individual "pixel" electrodes can be addressed, e.g., with row-column drivers as in an electro-optic display.

Figure 9:
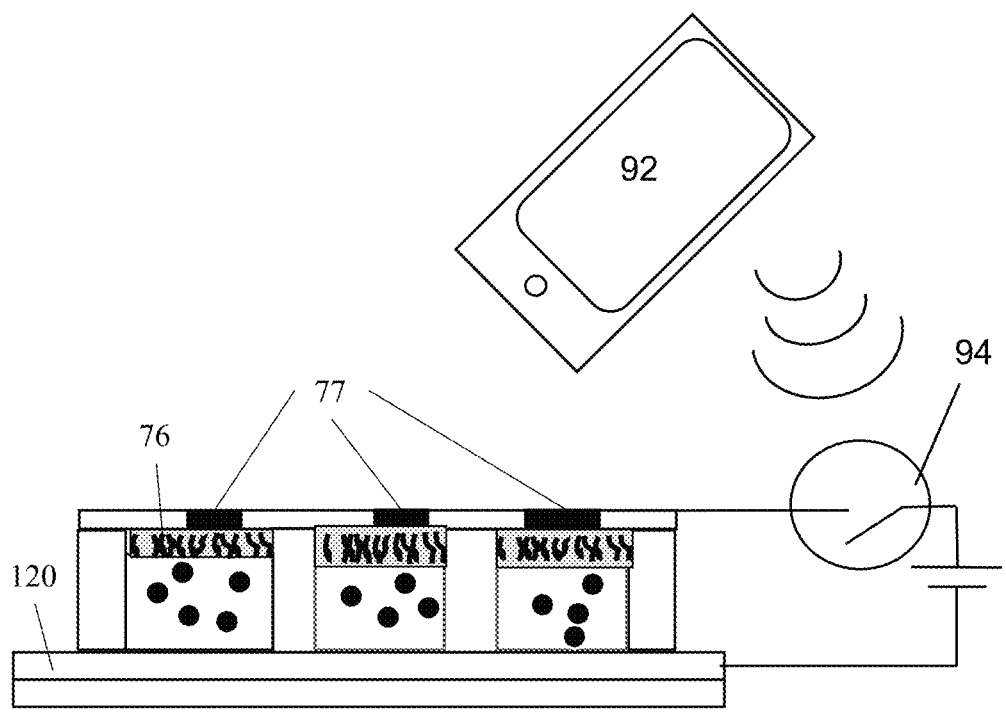
FIG. 9 illustrates an embodiment of a benefit agent delivery system including a plurality of microcells and a sealing layer comprising metallic material.
Figure 10:
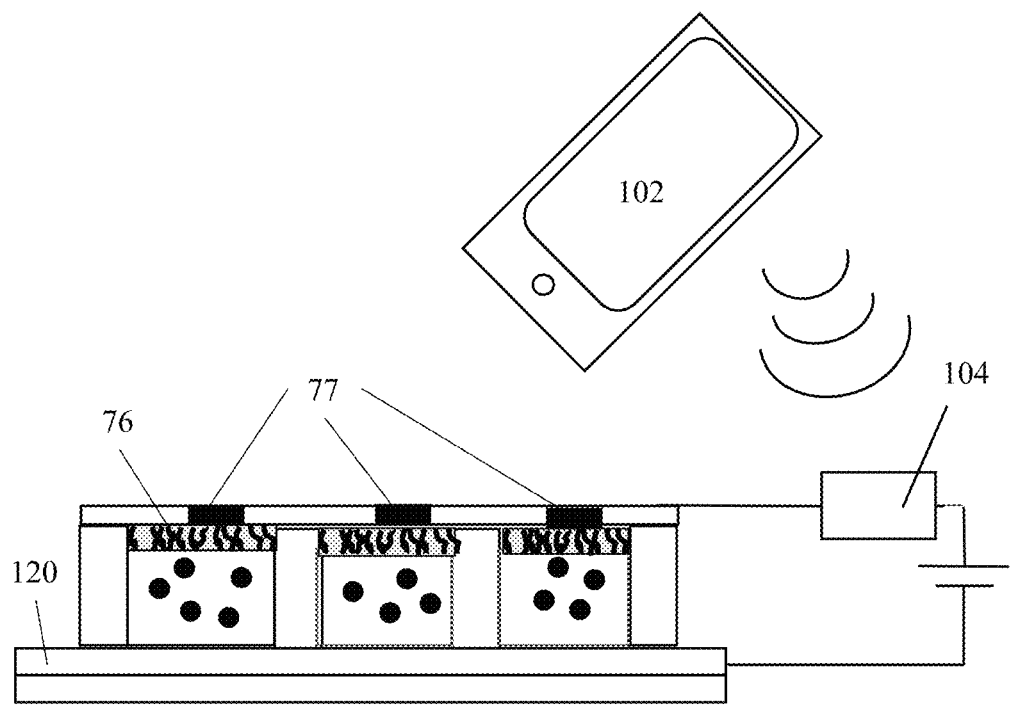
FIG. 10 illustrates an embodiment of a benefit agent delivery system including a plurality of microcells and a sealing layer comprising metallic material.

Advanced embodiments of a benefit agent delivery system will include circuitry to allow the benefit agent delivery system to be activated wirelessly with a secondary device 92, such as a smart phone or smart watch. As shown in FIG. 9, a simple system will allow a user to activate electronic/digital switch which will cause an electric field to open an electronic/digital switch 94, which will cause an electric field to be delivered, thereby causing the migration of the metallic material of the sealing layer and creating a porous sealing layer through which the benefit agent can be delivered at a desired surface or space and giving the user a dose of the benefit agents. In another embodiment, i.e., as shown in FIG. 10, the benefit agent delivery system includes a controller 104 that independently controls the plurality of the electrodes of the electrode layer. Controller 104 may also be able to receive wireless signals from a secondary device 102. The embodiment of FIG. 10 will allow a user to control, for example, the type of benefit agent that is delivered and the amount at the desired time. Using an application on the secondary device 102 it may be possible to program the benefit agent delivery system to modify the amount of benefit agent based upon the time of day. In other embodiments, the application may be operatively connected to biometric sensors, e.g., a fitness tracker, whereby the application causes the dosage to be turned off if, e.g., the pulse rate of the user exceeds a preset threshold.

When driving the benefit agent delivery systems of FIGS. 9 and 10, NFC, Bluetooth, WIFI, or other wireless communication function is turned on, allowing a user to manipulate the applied voltage across the microcells in order to activate the desired microcells. The activation can be initiated before or after the benefit agent delivery system is applied on the desired surface or location. In addition, benefit agent release adjustment can be achieved at any time when necessary. Because the microcell activation is controlled by smart watch or smart phone, the percentage and area for all of the microcells at different activation status is known, which means all of the usage data will be available to a user or a provider, including the time of the system activation and the amount of the benefit agent(s) administered. Thus, the system may provide a precise control to the user or another person (i.e. a doctor or health provider) to adjust the benefit agent delivery. Because every microcell can be activated independently, the system is programmable. That is, the overall benefit agent delivery can be programmed by activating each of the plurality of microcell when desired. For a benefit agent delivery system, which is designed to deliver benefit agents transdermally, the skin irritation can be mitigated because of the benefit agent can be controlled to be released over a period of time. Additionally, in drug delivery applications, patient compliance can be done effectively, because the smart device that is used to activate the system can remotely communicate with the physician for data sharing.

Figure 11:
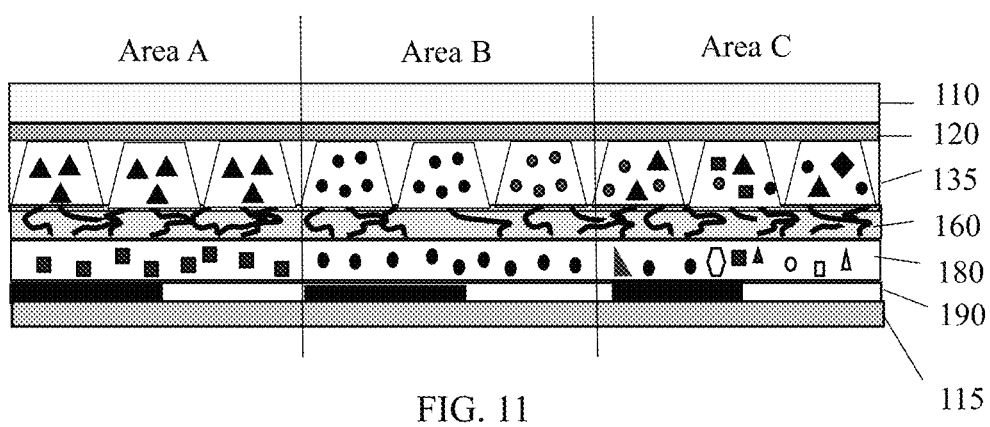
FIGS. 11 and 12 illustrate an embodiment of a benefit agent delivery system wherein the benefit agents are not only loaded into the microcells, but also in other layers such as an adhesive layer and/or a benefit agent loading layer. Different combinations of benefit agents can be included in different areas of the delivery system.

It is to be understood that the invention is not limited to combinations of benefit agents in the microcell, as different benefit agents can be delivered by adding those benefit agents to additional layers of the benefit agent delivery system. FIG. 11 exemplifies a benefit agent delivery system that comprises in order, a backing layer 110, a conductive layer 120, a plurality of microcells layer 135, a sealing layer comprising metallic material, an adhesive layer 180, an electrode layer, and a release sheet 115. As shown in FIG. 11, the benefit agents may be present in, for example, the adhesive layer.

Area A of FIG. 11 exemplified two different benefit agents being loaded into the plurality of microcell layer 135 and the adhesive layer 180. In some embodiments, the two benefit agents may be delivered at the same time. They may also have different delivery profiles. The system also provides a way to deliver different benefit agents with different physical properties, such as different hydrophobicities. For example, if the carrier of the microcell is polar, a hydrophilic benefit agent can be loaded into microcell at high loading. In this embodiment, the adhesive layer may include a hydrophobic benefit agent. Accordingly, the release profile of the two benefit agents can also be adjusted nearly independently. This system overcomes the problem of stabilizing a benefit agent with unfavorable solubility with, e.g., surfactants, capsules, etc.

Area B of FIG. 11 illustrates an embodiment in which the same benefit agent is loaded in both the microcells and the adhesive layer 180. Depending on the characteristics of the benefit agent, this method can help to load larger quantities of benefit agent into the benefit agent delivery system, which can help to increase the benefit agent release amount and control the release profile.

Area C of FIG. 11 illustrates an embodiment in which a combination of benefit agents is loaded either into the microcell, or into the adhesive layer 180, or into both layers. The benefit agents in the microcell composition and adhesive layer can be the same or different. The number of benefit agents in the microcell formulation and the number of benefit agents in the adhesive layer can also be the same or different.

Figure 12:
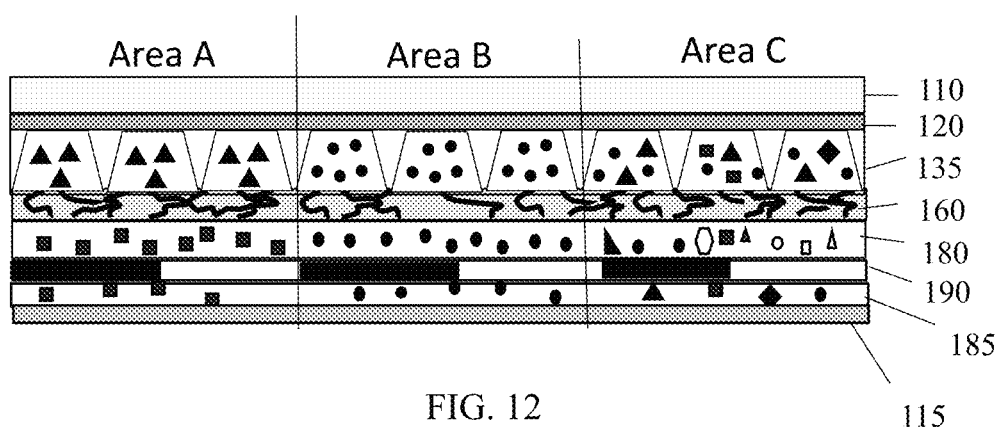

A benefit agent-loading layer 185 can be included into the benefit agent delivery system adjacent to the release sheet 115, as shown in FIG. 12. The amount and types of benefit agents in the benefit agent-loading layer 185 can be independent of the loading in the microcells and/or in the adhesive layer. The benefit agent can be introduced into only some portions of the adhesive layer, or it can present in both adhesive 180 and the benefit agent-loading layer 185. The benefit agent-loading layer 185 may be porous. In another example, the benefit-loading layer may be located between the sealing layer 160 and the adhesive layer 180.

The benefit agent delivery system may also comprise a porous diffusion layer or a rate control layer that is disposed between the sealing layer and the electrode layer. If there is an adhesive layer adjacent to the sealing layer, the porous diffusion layer or the rate control layer may be disposed between the adhesive layer and the electrode layer. The porous diffusion layer or the rate control layer and the adhesive layer may be integrated into one layer, which may have volume resistivity of less than $10^{-10}$ Ohm*cm, or less than $10^{-9}$ Ohm*cm. That is, the porous diffusion layer or the rate control layer may also serve as an adhesive layer, establishing an adhesive connection between the sealing layer and the electrode layer. The porous diffusion layer or the rate control layer and the electrode layer may also be integrated into one layer.

The porous diffusion layer may have average pore size larger than 0.2 nm. The rate control layer may have average pore size of 0.2 nm and smaller. The porous diffusion layer and the rate control layer may control the rate of the delivery of the benefit agent by its porosity, pore size, layer thickness, the chemical structure, and the polarity of the material from which it is constructed. Thus, for example, a rate control layer, positioned adjacent to the sealing layer or adjacent to the electrode layer, and made with a nonpolar polymer such as polyethylene having some porosity level may reduce the rate of delivery of relatively polar benefit agents, such as, for example benefit agents that are soluble or dispersible in water. In addition, a rate control layer having low porosity or higher thickness may slow down the delivery of benefit agents.

As mentioned above, various layers of the benefit agent delivery system may be combined or integrated in a single layer. For example, an adhesive layer an adjacent electrode layer may also be integrated into one layer. The same may be true for the combination of the porous diffusion layer or the rate control layer and the electrode layer, the combination of the sealing layer and the benefit agent-loading layer, the combination of the benefit agent-loading layer and the rate control layer, etc.

In an embodiment, the present invention is a method of operating a benefit agent delivery system. The benefit agent delivery system comprises (a) a conductive layer, (b) a plurality of microcells, wherein each microcell includes an opening and contains a carrier and a benefit agent, (c) a sealing layer spanning the opening of each microcell and comprising a polymeric material and a metallic material, (d) an electrode layer, and (e) a voltage source. The voltage source is coupled to the conductive layer and the electrode layer. The conductive layer, the microcell layer, the sealing layer and the electrode layer are vertically stacked upon each other. The microcell layer and the sealing layer are disposed between the conductive layer and the electrode layer. The conductive layer, the microcell layer, the sealing layer and the electrode layer may be vertically stacked upon each other in this order. Alternatively, the electrode layer, the microcell layer, the sealing layer and the conductive layer may be vertically stacked upon each other in this order. The method of operating the benefit agent delivery system comprises the steps of: providing the benefit delivery system and applying a voltage potential difference between the conductive layer and the electrode layer to generate an electric field; the electric field has a polarity causing the migration of the metallic material onto a surface of the microcell adjacent to the conductive layer. This removal of the metallic material of the sealing layer creates porosity to the sealing layer, enabling the delivery of the benefit agent. The method for operating a benefit agent delivery system may further comprise a step of controlling the rate of delivery of the benefit agent by the selection of the applied voltage potential. Higher voltage potential enables higher rate of release of the benefit agent by increasing the rate of removal of the metallic material from the sealing layer, reducing the time of the creation of its porosity.

EXAMPLE

On Demand Delivery of a Fragrance

Figure 13:
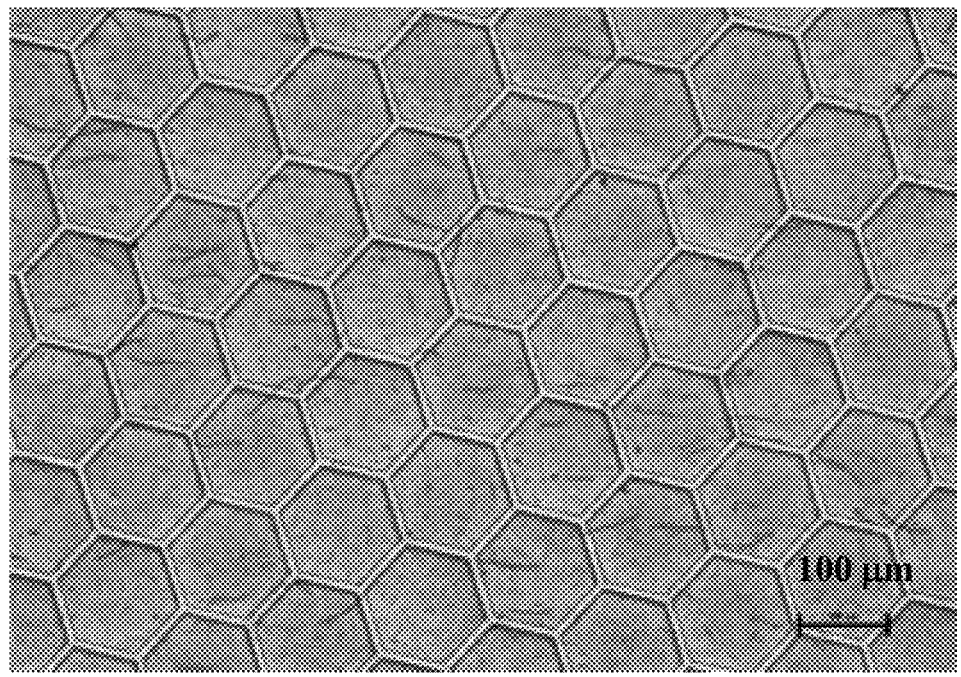
FIG. 13 is a microscopic image of the outside surface of a sealing layer of a benefit agent delivery system. The sealing layer comprises metal nanofibers.

A benefit agent delivery system that can be represented by FIG. 1A was constructed. The system comprised in order, a backing layer, a conductive layer, a plurality of microcells, a sealing layer, an adhesive layer, and an electrode layer. The conductive layer comprised an Indium-Tin oxide combination. The plurality of microcells comprised a medium composition (or internal phase) comprising 20 weight % of methyl salicylate fragrance in 80 weight % of triethyl citrate solvent. The microcells were sealed using a polymeric composition comprising 10 weight % of silver metal nanofibers by weight of the sealing layer. The silver nanofibers have an average diameter of 40 nm and an average length of 15 μm. FIG. 13 is a microphotograph of the sealing layer comprising the silver nanofibers, acquired after the microcells were sealed. A porous electrode layer comprising a plurality of electrodes was first coated with an adhesive composition, and laminated on the sealing layer. The conductive layer was electrically connected to the electrode layer and a voltage source. A voltage of 40 V was applied for 4 minutes on the left half part of the benefit agent delivery system. The voltage was applied so that the electrode layer was the anode (positive polarity) and the conductive layer was the cathode (negative polarity). Seven panelists evaluated the system by smelling the system from a distance of 30 cm before and after the application of the voltage. They ranked the benefit agent delivery system by using a four point scale, as follows:
- 3: A strong fragrance odor was sensed after the activation in comparison to the odor before the activation.
- 2: A moderate fragrance odor was sensed after the activation in comparison to the odor before the activation.
- 1: Very slight fragrance odor was sensed after the activation in comparison to the odor before the activation.
- 0: No difference in odor was sensed after the activation in comparison to the odor before the activation.

The average score for the seven panelist was 2.6. Thus, the panelists sensed that there was a significant odor of the fragrance after the activation of the system in comparison to the odor before the activation.

Figure 14A:
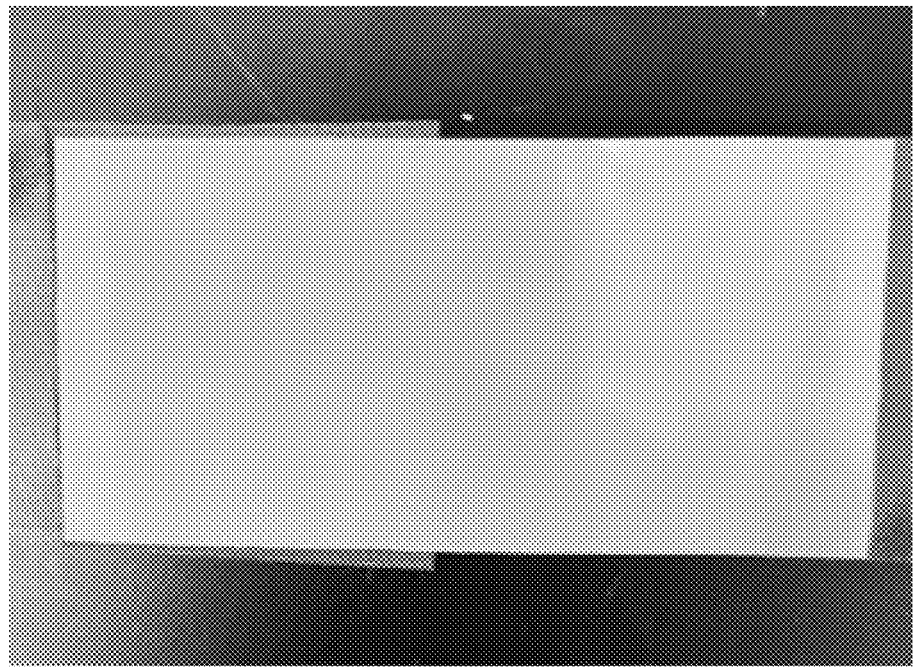
FIG. 14A is a photographic image of the outside surface of a plurality of microcells of a benefit delivery system before application of electrical field across the system; the image represents the outside surface of the plurality of the microcells opposite from the sealing layer.
Figure 14B:
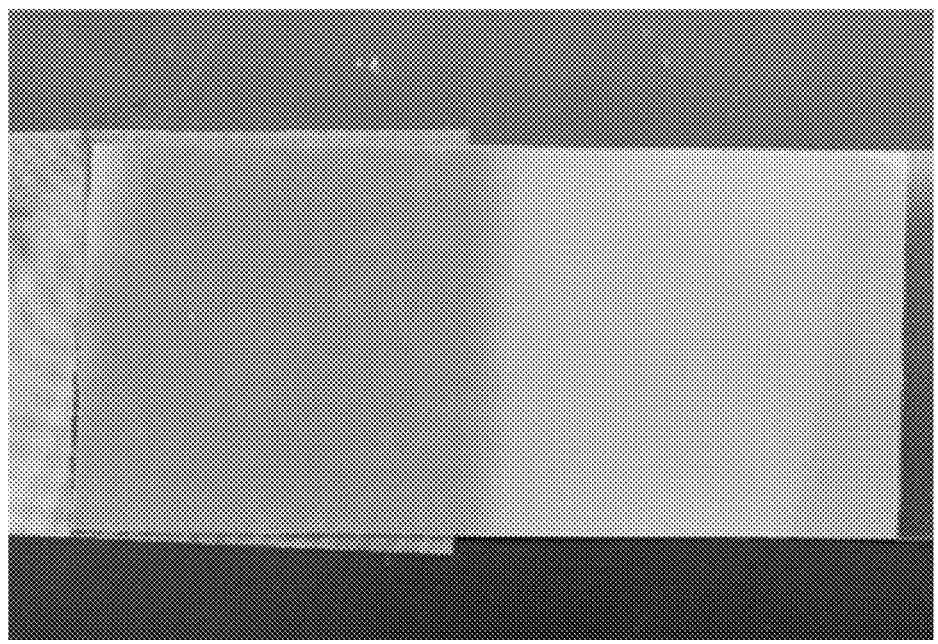
FIG. 14B is a photographic image of the outside surface of a plurality of microcells of a benefit delivery system after application of electrical field across the system; the image represents the outside surface of the plurality of the microcells opposite from the sealing layer; the electrical field is applied on the left side of the benefit agent delivery system; no electrical field was applied at the right side.

Photographic images of the constructed benefit agent delivery system were acquired from the side of the backing layer before (FIG. 14A) and after (FIG. 14B) the application of the electric field. In FIG. 14B, only the left side of the delivery system was activated. No voltage was applied on the right part of the delivery system. Both the image of FIG. 14A and the right side of the image of FIG. 14B, show that that the backing layer has a light yellow color. On the contrary, the left part of FIG. 14B, corresponding to the part of the system that was activated, is dark gold. The darker color was attributed to a metallic silver layer deposited on the inside surface of the microcells adjacent to the conductive layer of the activated microcells. This is evidence that the silver nanofibers, which were present in the sealing layer before the activation, migrated from the sealing layer and deposited as metallic layer near the cathode.

Figure 15A:
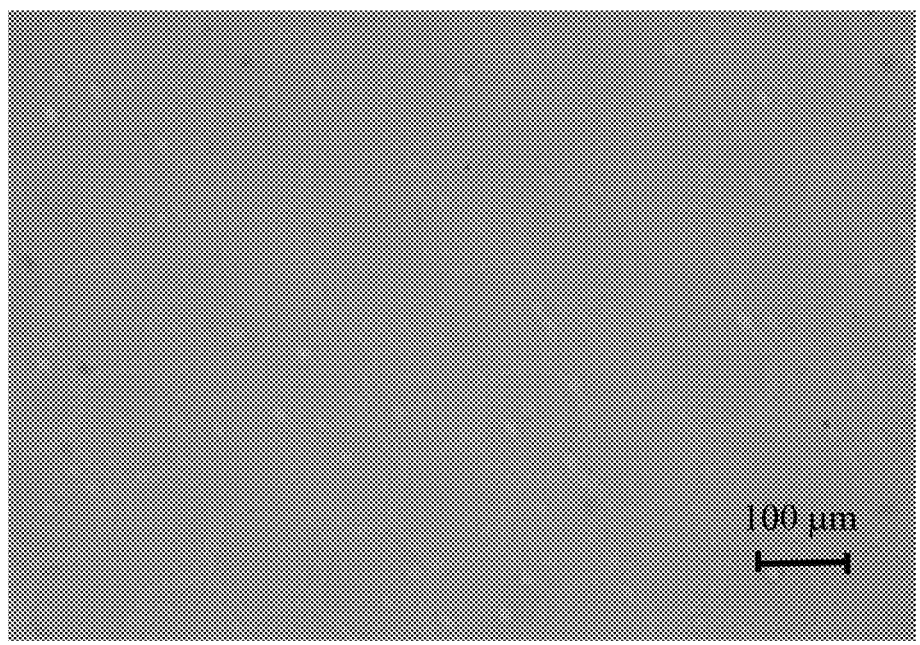
FIG. 15A is a microscopic image of the inside surface of a plurality of microcells of a benefit delivery system before application of electrical field across the system; the image was acquired after the removal of the sealing layer.
Figure 15B:
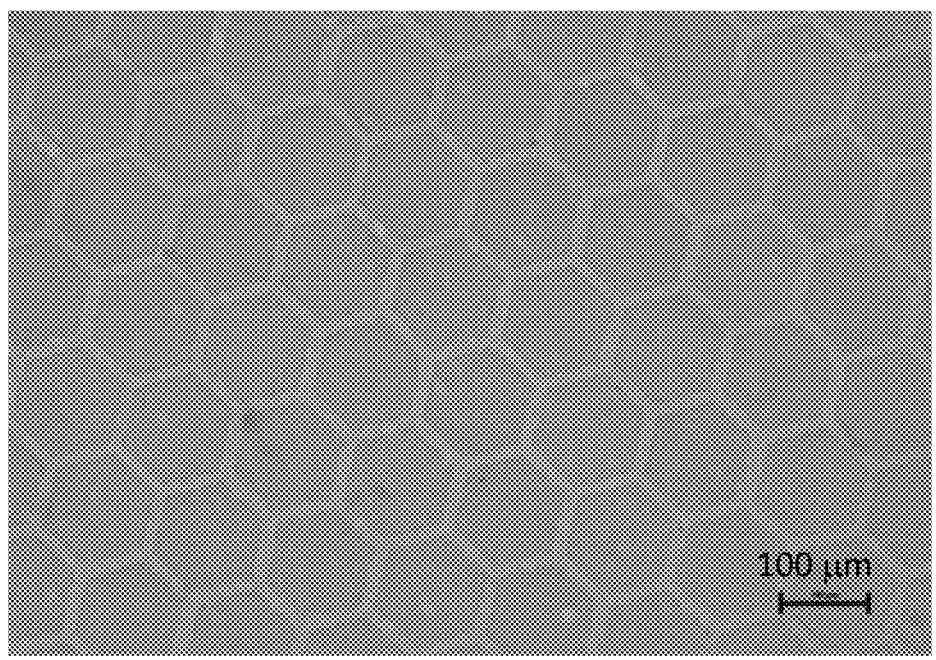
FIG. 15B is a microscopic image of the inside surface of a plurality of microcells of a benefit delivery system after application of electrical field across the system; the image was acquired after the removal of the sealing layer.

FIGS. 15A and 15B are microphotographs of the non-activated and activated microcells, respectively. More specifically, after the application of the voltage at the benefit agent delivery system as described above, the sealing layer was removed and microphotographs of the microcell layer were acquired looking from the opening of the microcells. The image of FIG. 15A corresponds to the inside surface of the non-activated microcells and the image of FIG. 15B corresponds to the inside surface of the activated microcells. The hexagonal shape of the microcells in the case of the non-activated portion is barely visible. On the contrary, the hexagonal shape of the microcells in the case of the activated portion is distinctly visible, because the deposition of the silver on the surface of the microcells increases the contrast between the surface of the microcell adjacent to the conductive layer and the walls of the microcells. This is another strong indication that the silver nanofibers, which were present in the sealing layer before the activation, migrated from the sealing layer and deposited on the inside surface of the microcells adjacent to the conductive layer. This process created a porous sealing layer through which the fragrance material was delivered in the vicinity of the benefit agent delivery system and was detected as fragrance odor by the panelists.

Thus, the invention provides for a benefit agent delivery system including a plurality of microcells, which include a carrier and a benefit agent, and a sealing layer comprising a metallic material in a polymer. Application of a voltage on the system results in the migration of the metallic material of the sealing and the creation of a porous sealing layer. The porosity of the sealing layer permits for the benefit agent to be delivered from the benefit agent delivery system. This disclosure is not limiting, and other modifications to the invention, not described, but self-evident to one of skill in the art, are to be included in the scope of the invention.

The invention claimed is:
1. A method for operating a benefit agent delivery system comprising the steps of:
   providing a benefit agent delivery system comprising (a) a conductive layer, (b) a plurality of microcells, each microcell including an opening and containing a carrier and a benefit agent, (c) a sealing layer spanning the opening of each microcell and comprising a polymeric material and a metallic material, (d) an electrode layer; and (e) a voltage source; wherein the conductive layer, the microcell layer, the sealing layer and the electrode layer are vertically stacked upon each other; wherein the microcell layer and the sealing layer are disposed between the conductive layer and the electrode layer; and wherein the voltage source is coupled to the conductive layer and the electrode layer;
   applying a voltage potential difference between the conductive layer and the electrode layer to generate an electric field having a polarity causing oxidation of the metallic material, removal of the metallic material from the sealing layer, and migration of the metallic material onto a surface of the microcell adjacent to the conductive layer.

2. The method for operating a benefit agent delivery system according to claim 1, further comprising a step of controlling the rate of delivery of the benefit agent by the selection of the applied voltage potential.

3. The method for operating a benefit agent delivery system according to claim 1, wherein the conductive layer, the microcell layer, the sealing layer and the electrode layer are vertically stacked upon each other in this order, and wherein the electrode layer is porous.

4. The method for operating a benefit agent delivery system according to claim 1, wherein the polymeric material of the sealing layer is selected from the group consisting of an acrylate, a methacrylate, a polycarbonate, a polyvinyl alcohol, cellulose, poly(N-isopropylacrylamide) (PNIPAAm), polylactic-co-glycolic acid) (PLGA), polyvinylidene chloride, acrylonitrile, amorphous nylon, oriented polyester, terephthalate, polyvinyl chloride, polyethylene, polypropylene, polystyrene, polyurethane, and alginate.

5. The method for operating a benefit agent delivery system according to claim 1, wherein the metallic material of the sealing layer is selected from the group consisting of metal particles, metal wires, metal fibers, metal flakes, metal rods, metal aggregates, and metal disks.

6. The method for operating a benefit agent delivery system according to claim 1, wherein the metallic material of the sealing layer comprises silver, copper, gold, platinum, zinc, chromium, nickel or combination thereof.

7. The method for operating a benefit agent delivery system according to claim 1, wherein the sealing layer further comprises a conductive material selected from the groups consisting of carbon black, carbon nanotubes, graphene, a dopant, and a conductive polymer.

8. The method for operating a benefit agent delivery system according to claim 1, wherein the carrier is selected from the group consisting of a liquid, a semi-solid, a gel and combinations thereof.

9. The method for operating a benefit agent delivery system according to claim 1, wherein the carrier is selected from a group comprising water, an organic compound, a silicone compound, and a combination thereof.

10. The method for operating a benefit agent delivery system according to claim 1, wherein the plurality of microcells comprises a benefit agent selected from the group consisting of a pharmaceutical agent, a vaccine, an antibody, a hormone, a protein, a nucleic acid, a nutraceutical agent, a nutrient, a cosmetic agent, a fragrance, a malodor removing agent, an agricultural agent, an air care agent, an anti-microbial agent, and a preservative.

11. The method for operating a benefit agent delivery system according to claim 1, wherein the sealing layer further comprises a benefit agent.

12. The method for operating a benefit agent delivery system according to claim 1, wherein the sealing layer and the electrode layer are integrated into one layer.

13. The method for operating a benefit agent delivery system according to claim 3, further comprising a porous diffusion layer or a rate control layer between the sealing layer and the electrode layer.

14. The method for operating a benefit agent delivery system according to claim 13, wherein the electrode layer and the porous diffusion layer are integrated into one layer.

15. The method for operating a benefit agent delivery system according to claim 3, further comprising an adhesive layer disposed between the sealing layer and the electrode layer.

16. The method for operating a benefit agent delivery system according to claim 15, further comprising a porous diffusion layer disposed between the adhesive layer and the electrode layer.

17. The method for operating a benefit agent delivery system according to claim 16, wherein the porous diffusion layer and the adhesive layer are integrated in one layer, and wherein the integrated layer has volume resistivity of less than $10^{-10}$ Ohm*cm.

* * * * *